(12) United States Patent
Keller et al.

(10) Patent No.: US 7,566,341 B2
(45) Date of Patent: Jul. 28, 2009

(54) MULTIPLE LUMEN HEAT EXCHANGE CATHETERS

(75) Inventors: Wade A. Keller, San Jose, CA (US); Timothy R. Machold, Moss Beach, CA (US)

(73) Assignee: ZOLL Circulation, Inc., Sunnyvale, CA (US)

(*) Notice: Subject to any disclaimer, the term of this patent is extended or adjusted under 35 U.S.C. 154(b) by 34 days.

(21) Appl. No.: 10/442,483

(22) Filed: May 21, 2003

(65) Prior Publication Data

US 2003/0195597 A1 Oct. 16, 2003

Related U.S. Application Data

(63) Continuation of application No. 09/777,612, filed on Feb. 6, 2001, now Pat. No. 6,610,083, and a continuation-in-part of application No. 09/489,142, filed on Jan. 21, 2000, now Pat. No. 6,428,563, and a continuation-in-part of application No. 09/138,830, filed on Aug. 24, 1998, now Pat. No. 6,620,188.

(60) Provisional application No. 60/181,249, filed on Feb. 9, 2000.

(51) Int. Cl.
*A61F 7/00* (2006.01)
(52) U.S. Cl. .................. 607/105; 607/106; 607/113
(58) Field of Classification Search ............ 606/20–1, 606/24, 190, 192, 27–52; 607/104–107
See application file for complete search history.

(56) References Cited

U.S. PATENT DOCUMENTS

| | | | |
|---|---|---|---|
| 4,038,519 A | 7/1977 | Foucras | 219/301 |
| 4,762,130 A | 8/1988 | Fogarty et al. | 128/348.1 |
| 5,151,100 A | 9/1992 | Abele et al. | 606/28 |
| 5,181,911 A | 1/1993 | Shturman | 604/96 |
| 5,250,070 A | 10/1993 | Parodi | 600/194 |
| 5,252,159 A * | 10/1993 | Arney | 156/169 |
| 5,295,995 A | 3/1994 | Kleiman | 606/194 |
| 5,308,356 A | 5/1994 | Blackshear, Jr. et al. | 606/194 |
| 5,342,301 A * | 8/1994 | Saab | 604/103.13 |
| 5,383,856 A * | 1/1995 | Bersin | 604/101.01 |
| 5,415,634 A * | 5/1995 | Glynn et al. | 604/103.08 |
| 5,458,575 A * | 10/1995 | Wang | 604/101.02 |
| 5,486,208 A * | 1/1996 | Ginsburg | 607/106 |
| 5,501,667 A * | 3/1996 | Verduin, Jr. | 604/101.01 |
| 5,624,392 A | 4/1997 | Saab | 604/43 |

(Continued)

FOREIGN PATENT DOCUMENTS

WO    PCT/US99/13516    12/1999

(Continued)

*Primary Examiner*—Roy D Gibson
(74) *Attorney, Agent, or Firm*—Robert D. Buyan; Stout, Uxa, Buyan & Mullins

(57) ABSTRACT

Catheter devices and methods for intravascular heating and/or cooling of human or veterinary patients. The catheter devices generally comprise catheters having inflow and outflow lumens and at least one curvilinear balloon connected to the inflow and outflow lumens such that heat exchange fluid may be circulated through the balloon(s). The catheter is inserted into the vasculature and heated or cooled fluid is circulated through the balloon(s) to heat or cool blood flowing in heat-exchange proximity to the balloon(s), thereby affecting heating or cooling of all or a portion of the patient's body.

17 Claims, 12 Drawing Sheets

U.S. PATENT DOCUMENTS

| | | | | |
|---|---|---|---|---|
| 5,716,386 | A | | 2/1998 | Ward et al. .................. 607/106 |
| 5,795,325 | A | * | 8/1998 | Valley et al. ................. 604/509 |
| 5,837,003 | A | | 11/1998 | Ginsburg .................... 607/106 |
| 5,843,116 | A | * | 12/1998 | Crocker et al. ............... 606/192 |
| 5,855,546 | A | * | 1/1999 | Hastings et al. ................. 600/3 |
| 5,957,963 | A | * | 9/1999 | Dobak, III .................. 607/104 |
| 6,099,454 | A | * | 8/2000 | Hastings et al. ................. 600/3 |
| 6,126,684 | A | * | 10/2000 | Gobin et al. ................. 607/113 |
| 6,149,677 | A | | 11/2000 | Dobak, III .................. 607/106 |
| 6,161,049 | A | * | 12/2000 | Rudie et al. ................. 607/101 |
| 6,190,356 | B1 | * | 2/2001 | Bersin .................... 604/101.01 |
| 6,231,595 | B1 | | 5/2001 | Dobak, III .................. 607/106 |
| 6,261,312 | B1 | | 7/2001 | Dobak, III et al. ........... 607/105 |
| 6,287,326 | B1 | | 9/2001 | Pecor ......................... 607/105 |
| 6,497,721 | B2 | * | 12/2002 | Ginsburg et al. ............. 607/106 |
| 6,607,517 | B1 | * | 8/2003 | Dae et al. .................... 604/500 |

FOREIGN PATENT DOCUMENTS

WO     PCT/US99/08455     2/2000

* cited by examiner

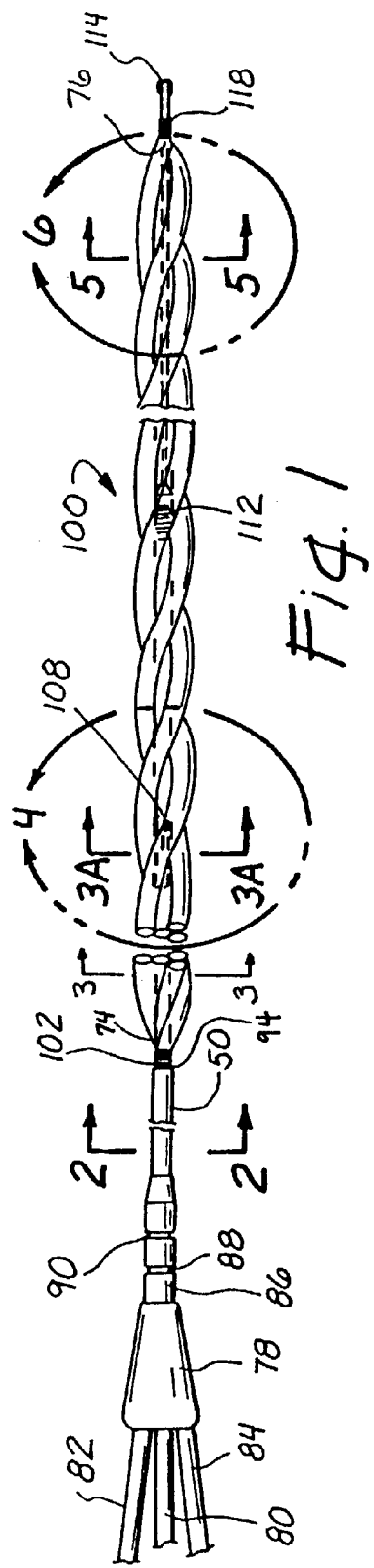
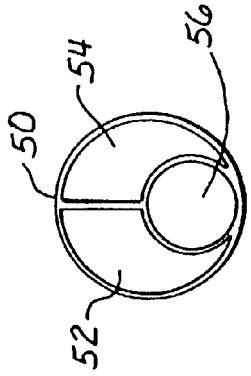
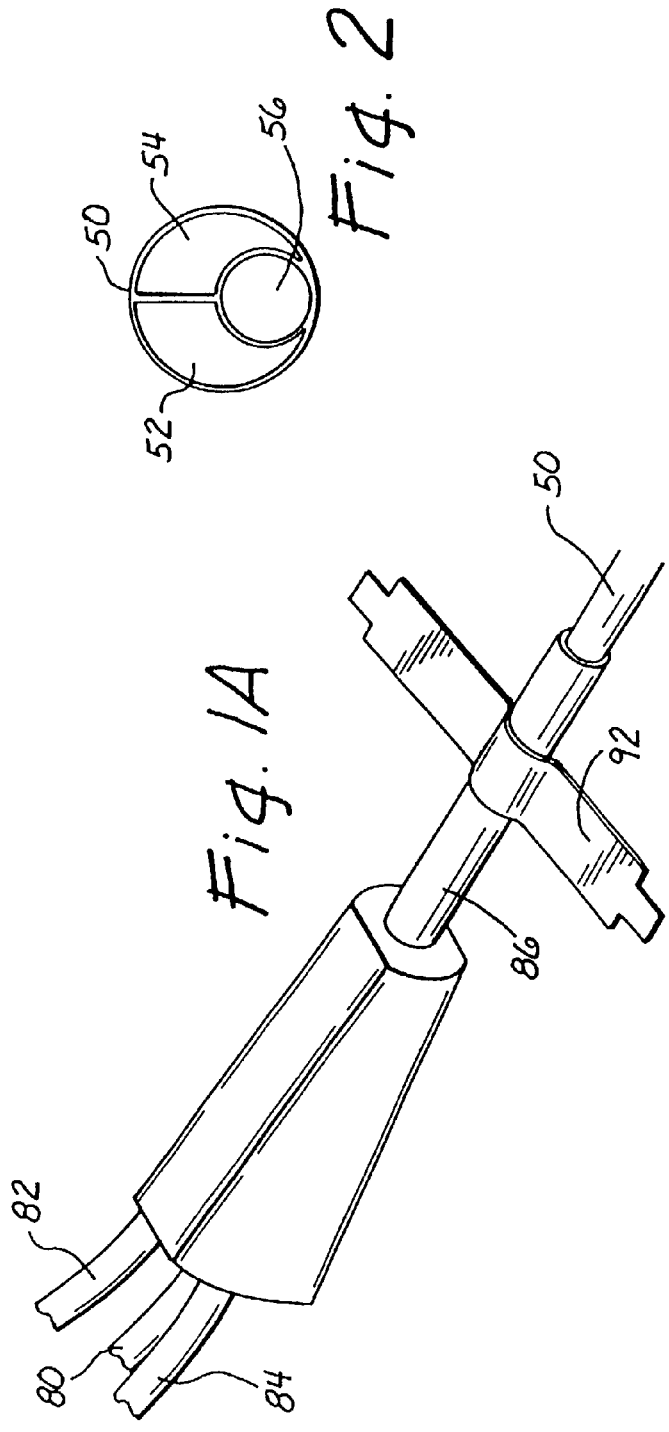

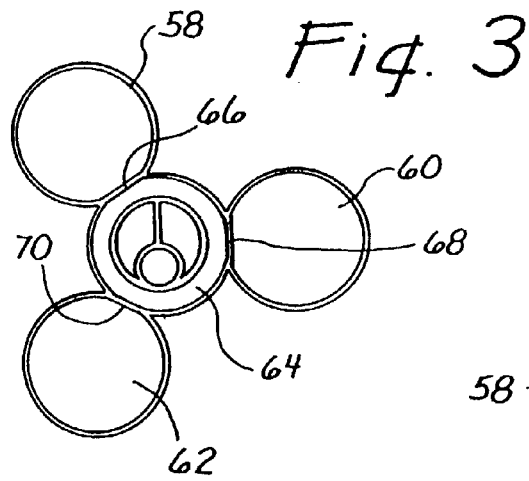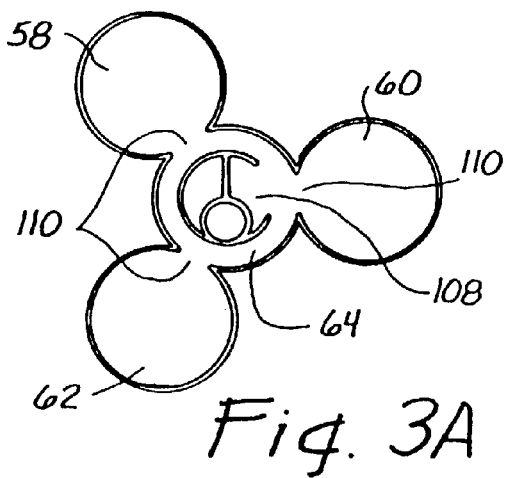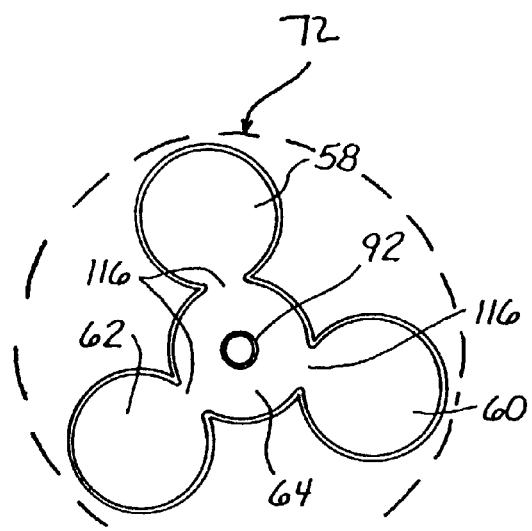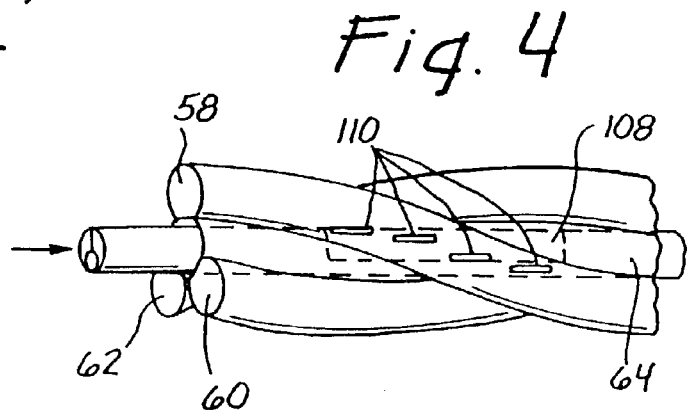

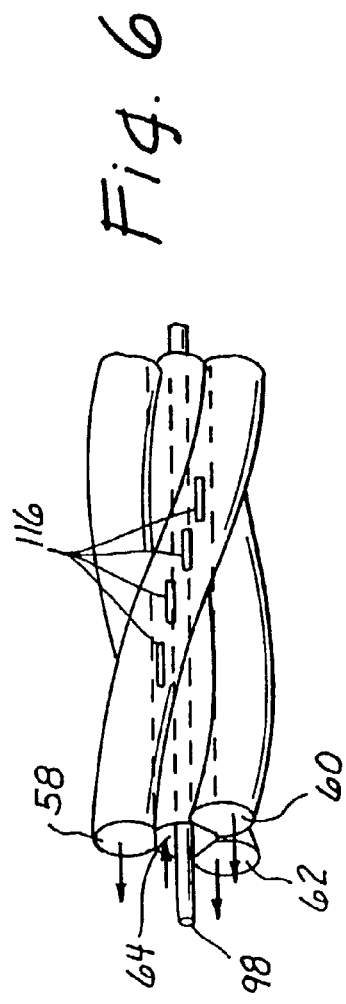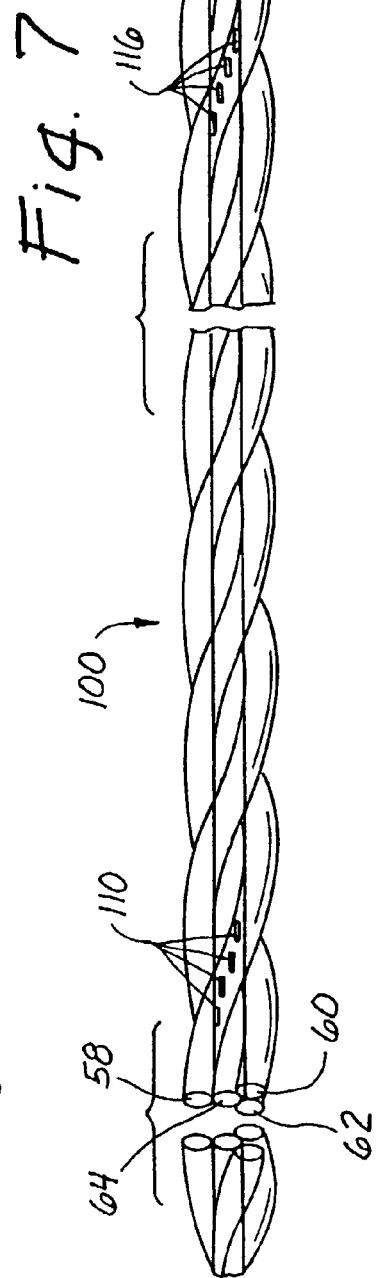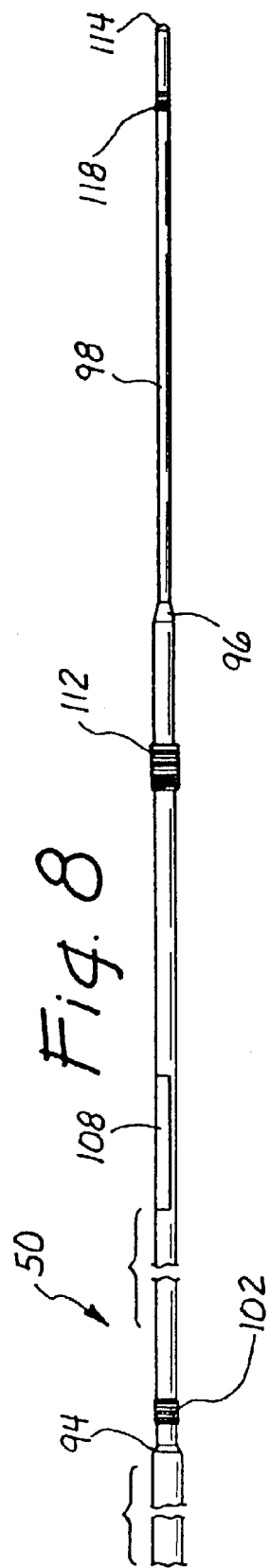

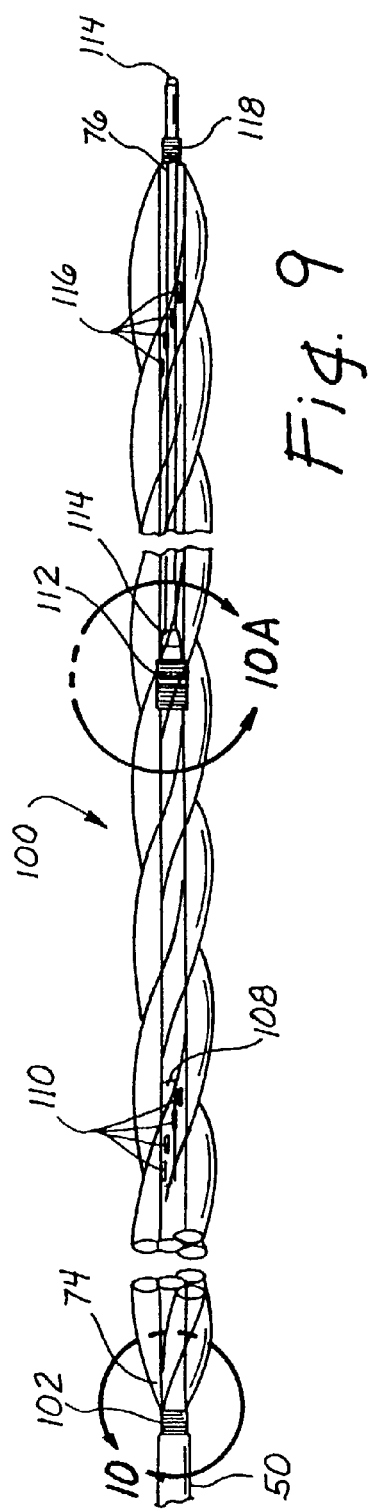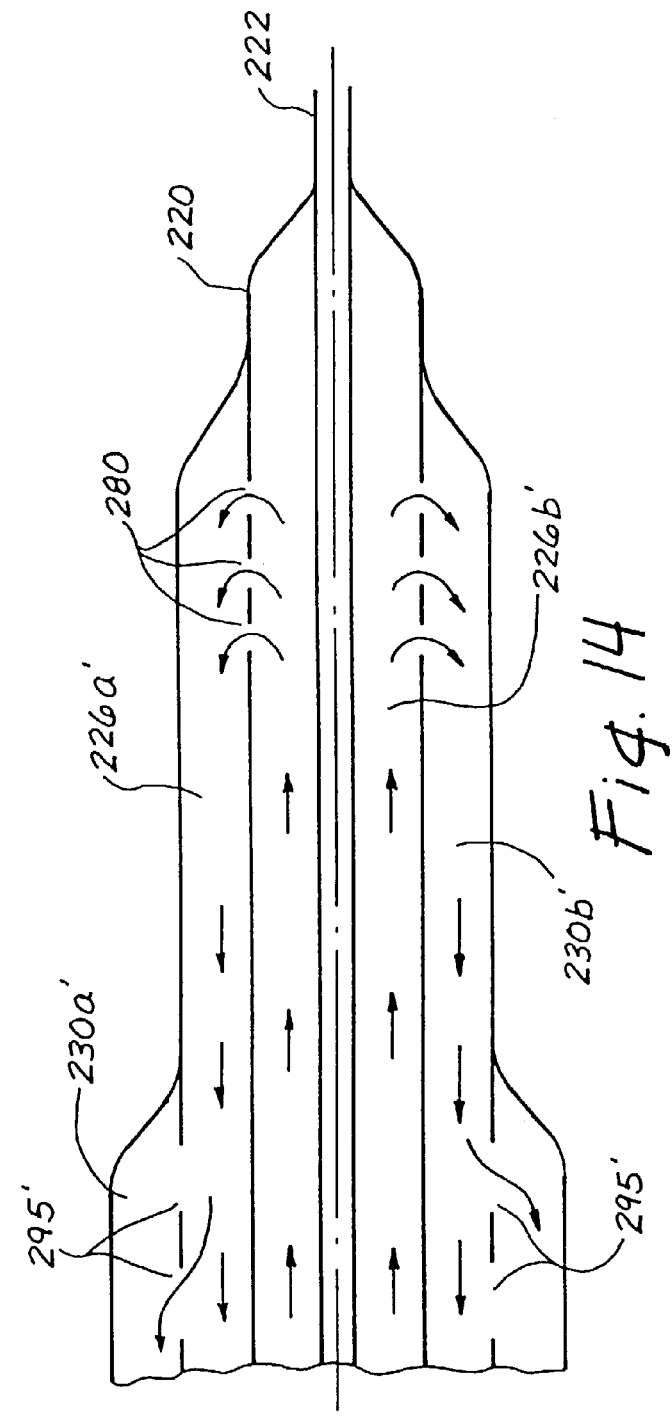

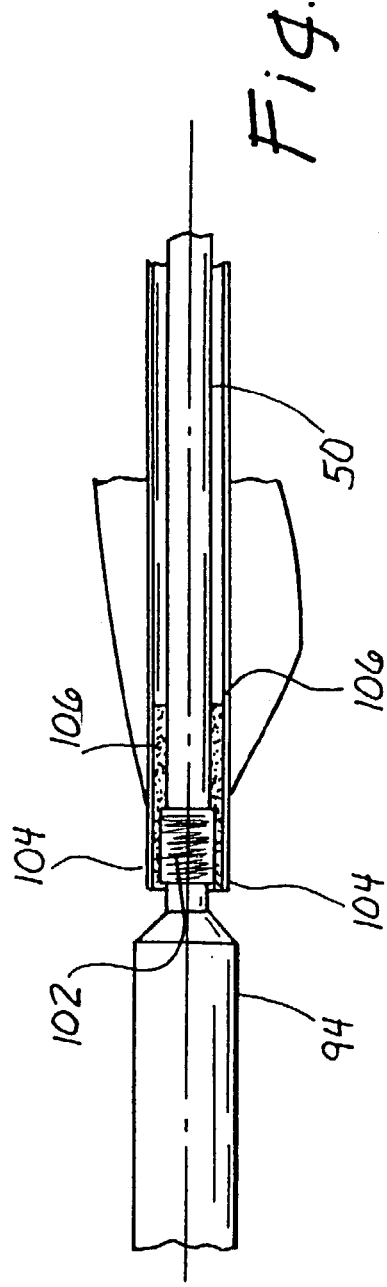
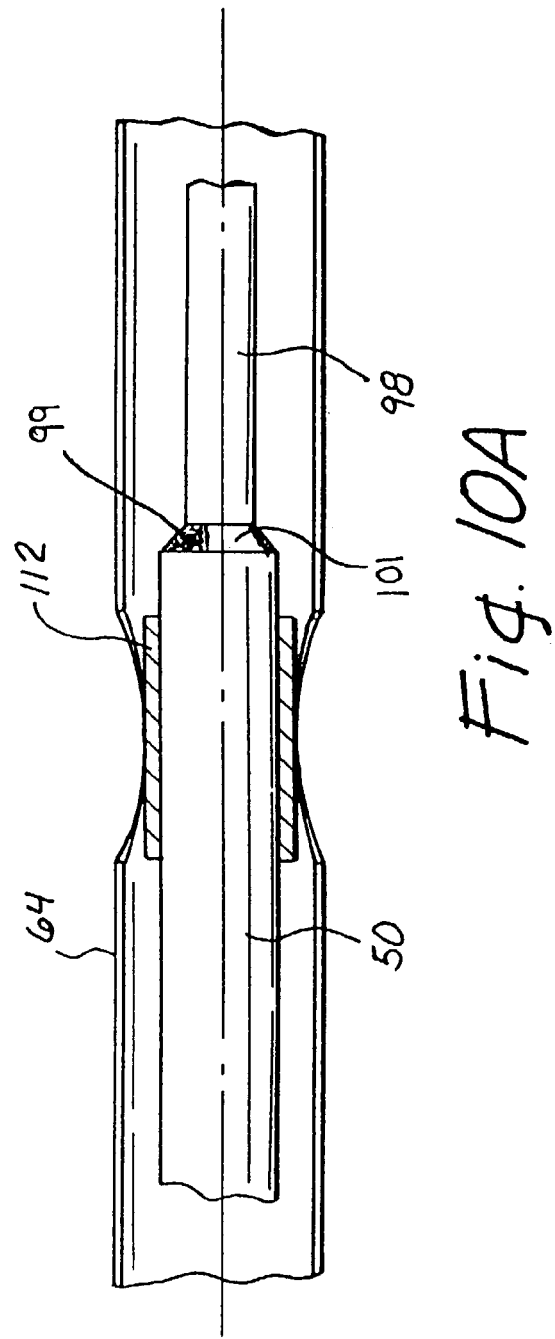

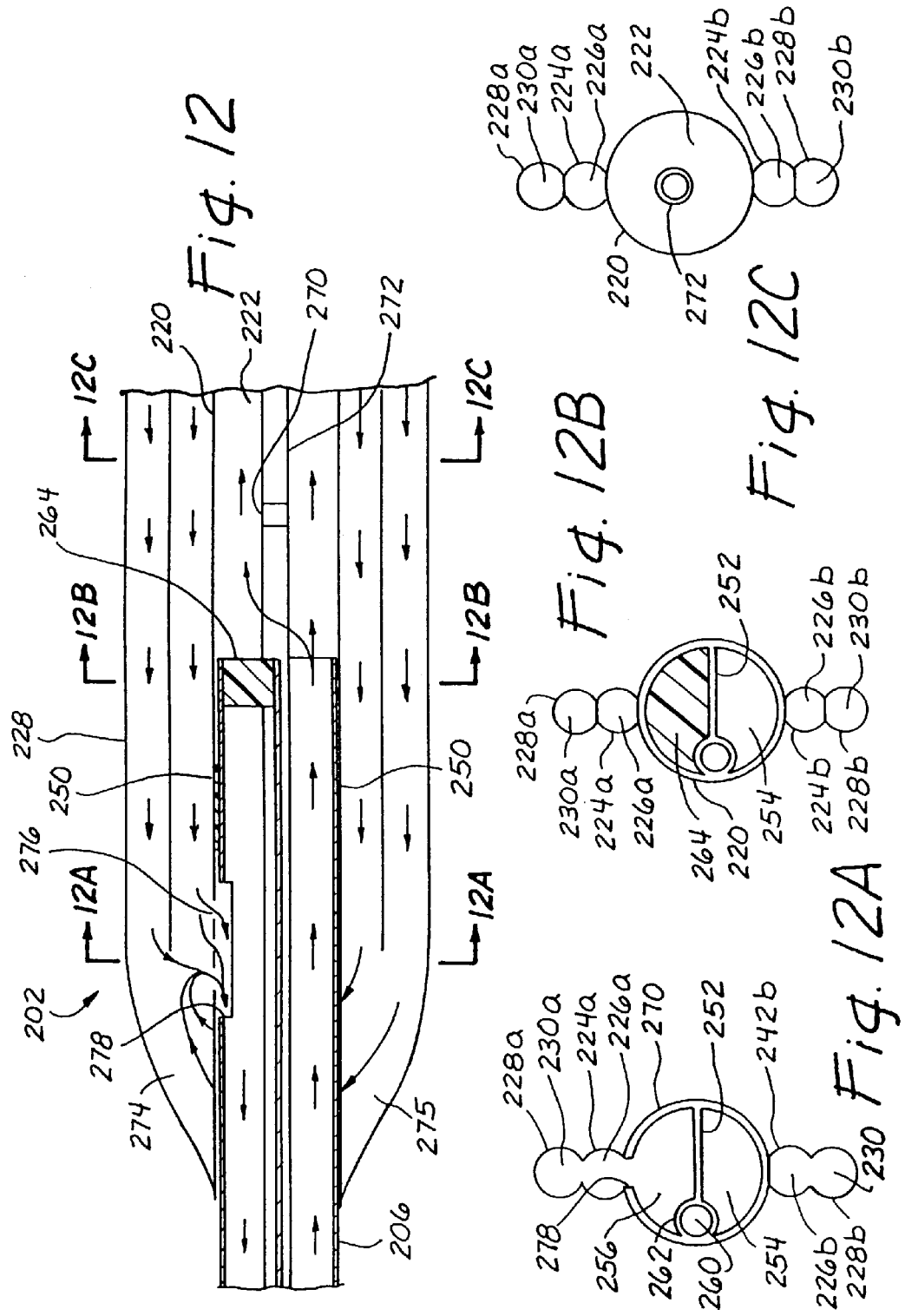

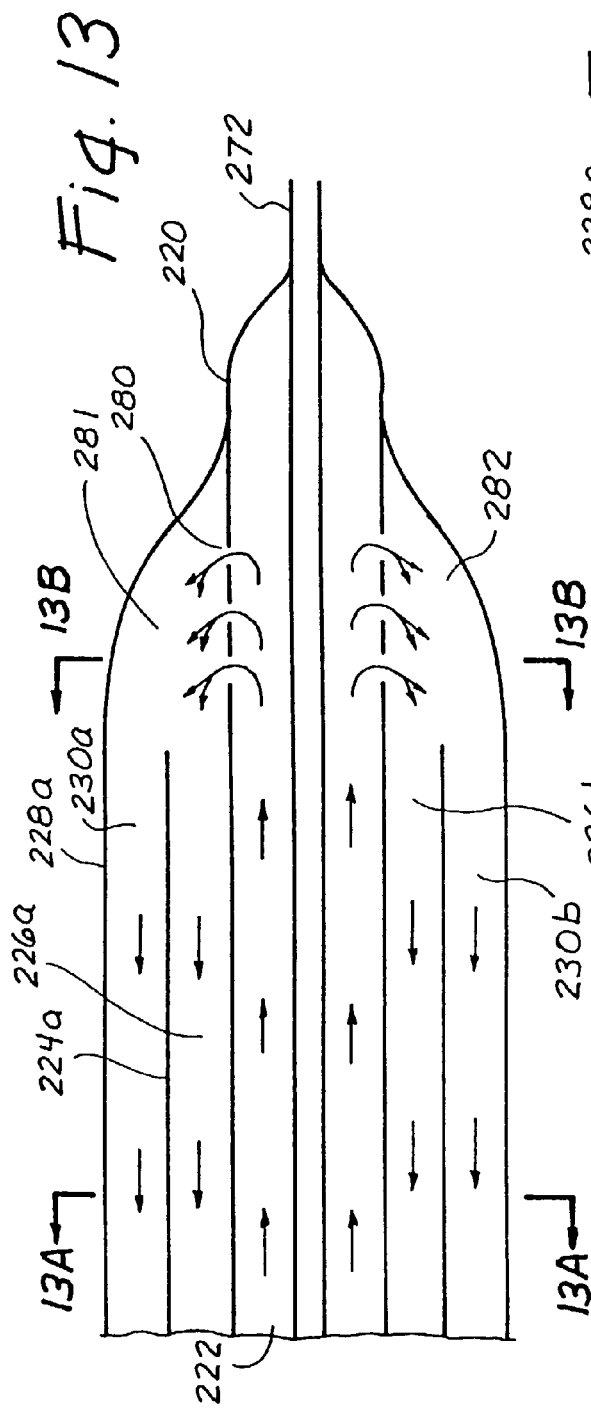
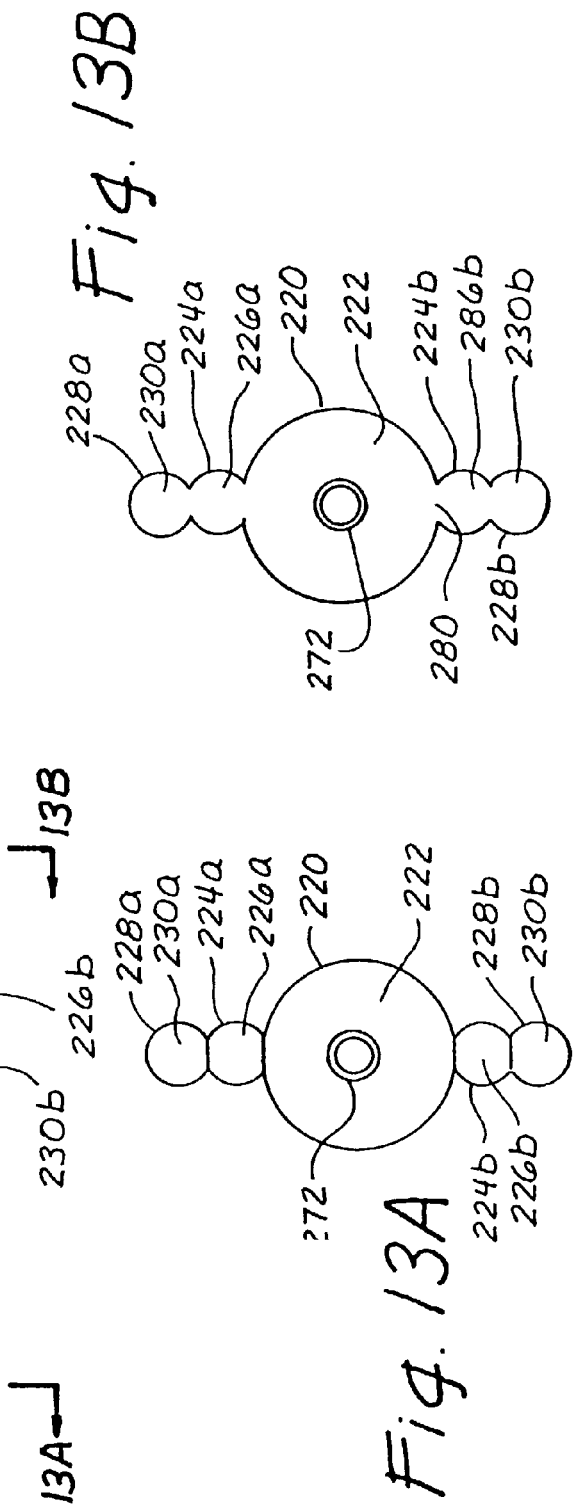

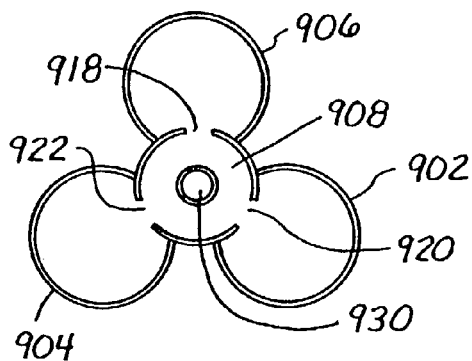
Fig. 15B
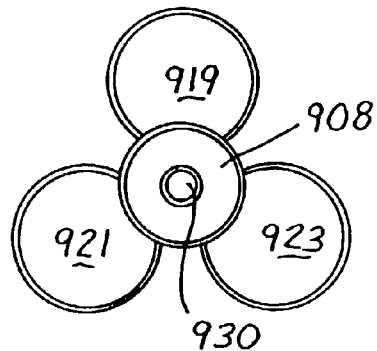
Fig. 15C
Fig. 15D
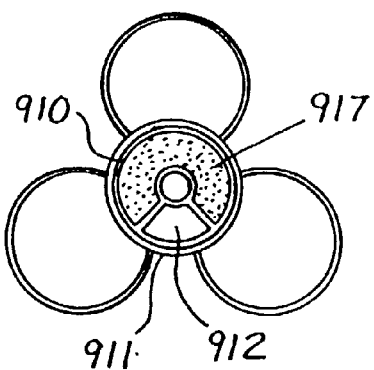
Fig. 15E
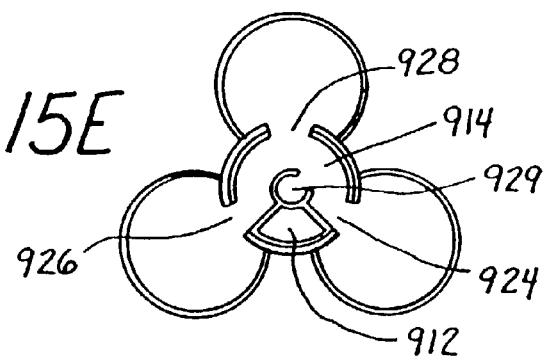
Fig. 15F
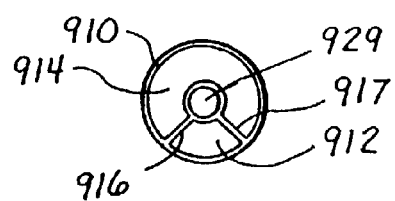

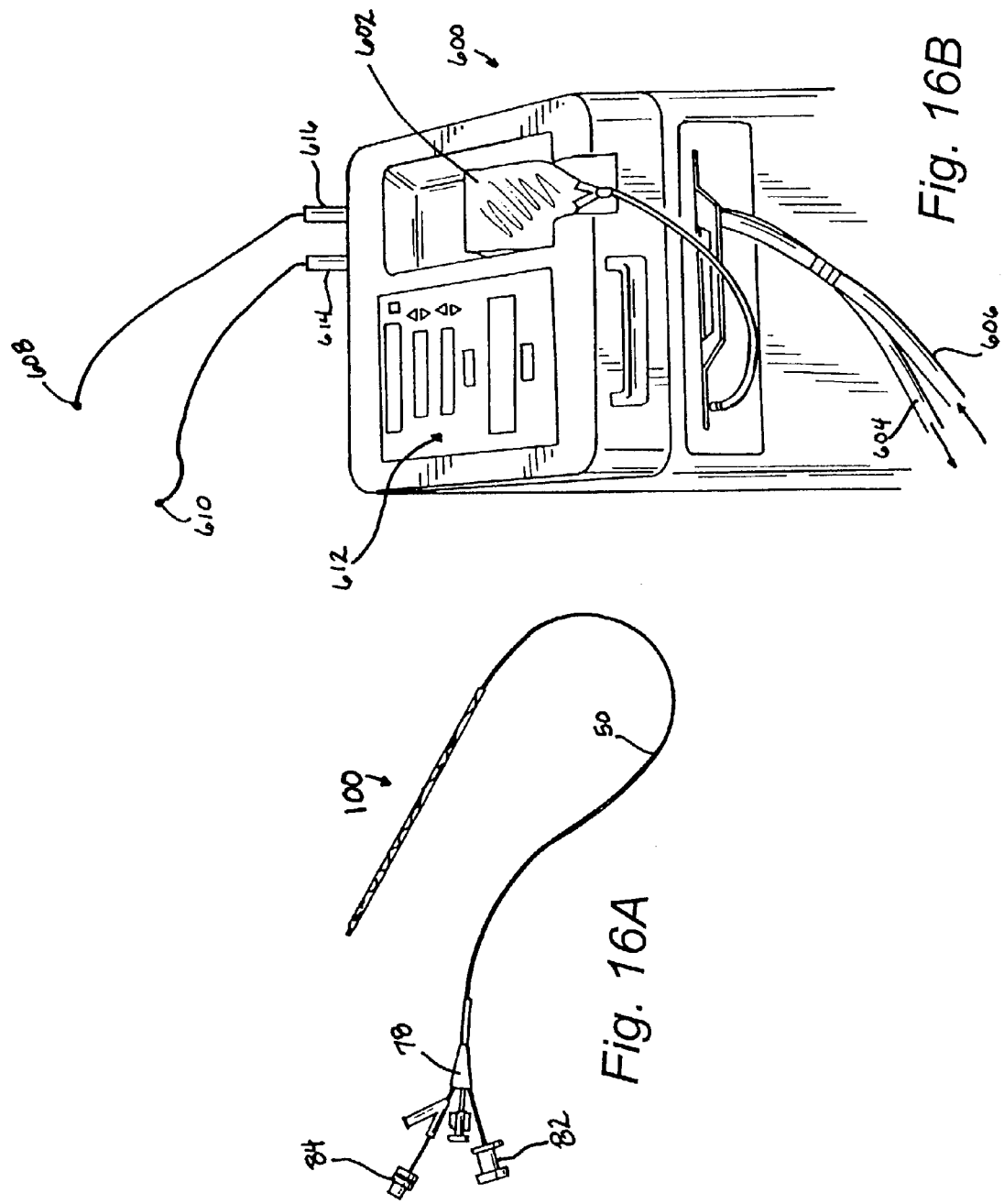

Fig. 17

```
┌─────────────────────────────────────────────────────────────────────┐
│ Inserting a multi-lumen heat exchange catheter with a heat exchange │
│ region having curvilinear heat exchange balloon elements            │
│ percutaneously so that the heat exchange region is located within   │
│ the vasculature of a patient with the heat exchange region in heat  │
│ exchanging proximity to the flowing blood of a patient              │
└─────────────────────────────────────────────────────────────────────┘
                                  ↓
┌─────────────────────────────────────────────────────────────────────┐
│ Circulating heat exchange fluid from an external heat exchange unit │
│ to the heat exchange region to control the temperature of the heat  │
│ exchange region                                                     │
└─────────────────────────────────────────────────────────────────────┘
                                  ↓
┌─────────────────────────────────────────────────────────────────────┐
│ Exchanging heat between the heat exchange region and the flowing    │
│ blood for a sufficient length of time to affect the temperature of  │
│ tissue of the patient                                               │
└─────────────────────────────────────────────────────────────────────┘
                                  ↓
┌─────────────────────────────────────────────────────────────────────┐
│ Providing a microprocessor which controls the external heat         │
│ exchanger and the source of heat exchange fluid for the catheter,   │
│ and inputting user parameters into a microprocessor which           │
│ parameters are temperature control parameters.                      │
└─────────────────────────────────────────────────────────────────────┘
                                  ↓
┌─────────────────────────────────────────────────────────────────────┐
│ Placing temperature sensors to sense the temperature of the patient │
│ and generate a signal based on the sensed temperature and directing │
│ said signals to said microprocessor                                 │
└─────────────────────────────────────────────────────────────────────┘
                                  ↓
┌─────────────────────────────────────────────────────────────────────┐
│ Controlling the temperature of the heat exchange fluid supplied by  │
│ the external heat exchange unit based on the temperature signal and │
│ the user input to achieve the user parameters.                      │
└─────────────────────────────────────────────────────────────────────┘
```

MULTIPLE LUMEN HEAT EXCHANGE CATHETERS

RELATED APPLICATIONS

This is a continuation of application Ser. No. 09/777,612 filed on Feb. 6, 2001 now U.S. Pat. No. 6,610,083, which was a continuation-in-part of application Ser. No. 60/181,249 filed on Sep. 2, 2000, continuation-in-part of application Ser. No. 09/138,830 filed on Aug. 24, 1998 now U.S. Pat. No. 6,620,188, Ser. No. 09/489,142 filed on Jan. 21, 2000 now U.S. Pat. No. 6,428,563.

FIELD OF THE INVENTION

This invention relates generally to medical devices and a method of using them for selectively affecting the temperature of a patient's body, or portion of the patient's body, by adding or removing heat from the patient's body fluid through the use of a heat exchange catheter with a heat exchange region in contact with the body fluid, the heat exchange region being shaped for maximum heat exchange with minimum insertion profile and minimum obstruction to the flow of the body fluid. More particularly, this invention relates to a heat exchange catheter with a heat exchange region which is an advantageously shaped balloon, wherein the balloon is placed in flowing body fluid and heat exchange fluid circulates within the balloon to add or remove heat from the body fluid in order to treat or induce whole body or regional hypothermia or hyperthermia. This invention also relates to a method of controlling the amount of heat removed or added by the heat exchange region to affect the temperature of all or part of the patient's body in response to a signal representing the temperature of all or part of a patient's body.

BACKGROUND OF THE INVENTION

Under ordinary circumstances, thermoregulatory mechanisms exist in the healthy human body to maintain the body at a constant temperature of about 37° C. (98.6° F.), a condition sometimes referred to as normothermia. Normothermia is generally a desirable condition, and to maintain normothermia, the thermoregulatory mechanisms act so that heat lost to the environment is replaced by the same amount of heat generated by metabolic activity in the body.

For various reasons, a person may develop a body temperature that is below normothermia, a condition known as hypothermia, or a temperature that is above normothermia, a condition known as hyperthermia. These conditions are generally harmful and are usually treated to reverse the condition and return the patient to normothermia. In certain other situations, however, they may be desirable and may even be intentionally induced.

Accidental hypothermia may result when heat loss to the environment exceeds the body's ability to produce heat internally or when a person's thermoregulatory ability has been lessened due to injury, illness or anesthesia. For example, a person exposed to a cold environment such as a hiker wandering in a very cold climate for too long, or a sailor overboard in cold water, may become dangerously hypothermic. Likewise, anesthesia generally disables a patient's thermoregulatory ability, and it is often the case that, during long surgery with significant exposure of the patient's internal body cavities, a patient becomes significantly hypothermic. Such hypothermia is generally harmful, and must be quickly reversed to restore the victim to health.

Simple methods for treating hypothermia have been known since very early times. Such methods include wrapping the patient in blankets, administering warm fluids by mouth, and immersing the patient in a warm water bath. If the hypothermia is not too severe, and the need to reverse the hypothermia is not too urgent, these methods may be effective. However, wrapping a patient in a blanket depends on the ability of the patient's own body to generate heat to re-warm the body. Administering warm fluids by mouth relies on the patient's ability to swallow, and is limited both in the temperature of the liquid consumed and the amount of fluid that may be administered in a limited period of time. Immersing a patient in warm water is often impractical, particularly if the patient is simultaneously undergoing surgery or some other medical procedure.

More recently, hypothermia may be treated by the application of a warming blanket that applies heat to the skin of the patient. Applying heat to the patient's skin, however, may be ineffective in providing heat to the core of the patient's body. Heat applied to the skin has to transmit through the skin by conduction or radiation which may be slow and inefficient, especially if the patient has a significant layer of fat between the warming blanket and the body's core.

Paradoxically, if the patient is suffering significant core hypothermia, the application of warmth to the patient's skin, whether by immersion in hot water or application of a warm blanket, may actually exacerbate the core hypothermia and may even induce shock. The body's thermoregulatory responses to cold that work to conserve heat in the body's core include vasoconstriction and arterio-venous shunting (AV shunts). Vasoconstriction occurs when the capillaries and other blood vessels in the skin and extremities constrict so that most of the blood pumped by the heart circulates within the core rather than through the skin and extremities. Similarly, in AV shunting, naturally occurring blood shunts exist between some arteries providing blood to capillary beds in the skin and extremities and veins returning blood from those capillary beds and extremities. When the body is cooled, the vessels in the capillary beds constrict, and the shunts may be opened, causing blood to by-pass those capillary beds altogether. Thus when the body is cold, the tissues in the extremities, and particularly at the surface, have little blood flowing to them and may become quite cold relative to the body's core temperature.

When heat is applied to the skin of such a patient, the temperature sensors in the skin may cause the vasoconstriction to reverse and the AV shunts to close. When this happens, blood from the core floods into the very cold tissue on the body surface and extremities, and as a result the blood loses heat to those tissues, often far more than the amount of heat being added by the surface warming. As a result, the victim's core temperature may plummet and the patient may even go into shock.

Partly in response to the inadequacies of surface application of heat, methods have been developed for adding heat to a patient's body by internal means. A patient being administered breathing gases, for example a patient under anesthesia, may have the breathing gases warmed. For some situations, particularly mild hypothermia requiring the addition of small amounts of heat, this method may be effective, but it is limited in the amount of heat that can be administered without injuring the lungs. Similarly, a patient receiving IV fluids may have the fluids warmed, or a bolus of warm fluid may be administered intravenously. Again, this may be effective in the case of mild hypothermia, but the amount of heat that may be added to a patient's body is limited because the temperature of the IV fluid is limited to a temperature that will not be destructive to the blood, generally thought to be about 41° C.-49° C., and the amount of fluid that is acceptable to administer to the patient.

A more invasive method may be used to add heat to a patient's blood, particularly in the case of heart surgery. A cannula is attached to a vein, usually the inferior vena cava (IVC) of a patient, the vein clamped off and virtually all the patient's blood shunted through the cannula to an external pump. The blood is then pumped back into the patient's body, generally to the arterial side of the patient's circulation. Blood removed from a patient may be heated or cooled externally before it is reintroduced into the patient's body. An example of such a by-pass arrangement is the Cardio-Pulmonary By-pass system (CPB) often used in open heart surgery.

This by-pass method, once it is initiated, is both fast and effective in adding or removing heat from a patient's blood and in exercising control over the patient's body temperature in general, but has the disadvantage of involving a very invasive medical procedure which requires the use of complex equipment, a team of highly skilled operators, is generally only available in a surgical setting, and because of these complexities, requires a long time to initiate. In fact, it generally cannot begin until after the patient's thorax has been surgically opened. For all these reasons, it is generally not useful for emergency treatment of hypothermia. By-pass also involves mechanical pumping of blood, which is generally very destructive to the blood resulting in cytotoxic and thrombolytic problems associated with removal of blood from the body, channeling the blood through various tubes, artificially oxygenating the blood, and returning the blood subjected to these stresses to the circulatory system, including the brain. Because of the potential harmful impact on the patient, most surgeons attempt to limit the time a patient is subjected to by-pass to less than four hours.

Methods for adding heat to the core of the body that do not involve pumping the blood with an external, mechanical pump have been suggested. For example, a method of treating or inducing hypothermia or hyperthermia by means of a heat exchange catheter placed in the bloodstream of a patient was described in U.S. Pat. No. 5,486,208 to Ginsburg, the complete disclosure of which is incorporated herein by reference. That patent discloses and claims a method of increasing a patient's body temperature by adding heat to the blood by inserting a heat exchange catheter having a balloon with heat exchange fins into the vascular system and circulating heat exchange fluid through the balloon while the balloon is in contact with the blood.

Although accidental hypothermia is generally harmful and requires treatment, in some instances it may be desirable to induce hypothermia or permit it to persist in a controlled situation. Hypothermia is generally recognized as being neuroprotective and may be induced for that reason. Neural tissue such as the brain or spinal cord, is particularly subject to damage by vascular disease processes including, but not limited to ischemic or hemorrhagic stroke, blood deprivation for any reason including cardiac arrest, intracerebral or intracranial hemorrhage, and head trauma. Other instances where hypothermia may be protective include treatment of myocardial infarction, and heart surgery, neurosurgical procedures such as aneurysm repair, endovascular aneurysm repair procedures, spinal surgeries, procedures where the patient is at risk for brain, cardiac or spinal schemia such as beating heart by-pass surgery or any surgery where the blood supply to the heart, brain or spinal cord may be temporarily interrupted. In each of these instances, damage to brain tissue may occur because of brain ischemia, increased intracranial pressure, edema or other processes, often resulting in a loss of cerebral function and permanent neurological deficits. Hypothermia may be intentionally induced because it is advantageous in such situations. In fact, in some of these situations, such as beating heart by-pass surgery, hypothermia currently occurs as a normal side effect of anesthesia disabling a patient's normal thermoregulatory responses in conjunction with prolonged exposure of the chest cavity. The resultant hypothermia may not itself be harmful if adequate control over the patient's temperature is established, and where the hypothermic condition is controlled as to depth and duration, it may be permitted to persist or even induced. Control of the depth of hypothermia and reversal of hypothermia after the operation are both important, and if that control is not possible, hypothermia is generally thought to be undesirable.

Although the exact mechanism for neuroprotection is not fully understood, lowering the brain temperature is believed to effect neuroprotection through several mechanisms including, the blunting of any elevation in the concentration of neurotransmitters (e.g., glutamate) occurring after ischemic insult, reduction of cerebral metabolic rate, moderation of intracellular calcium transport/metabolism, prevention of ischemia-induced inhibitions of intracellular protein synthesis and/or reduction of free radical formation as well as other enzymatic cascades and even genetic responses.

Besides its benefit as a prophylactic measure, for example during surgery to prevent damage in case of neurologic ischemia, it is also sometimes desirable to induce whole-body or regional hypothermia for as a treatment in response to certain neurological diseases or disorders such as head trauma, spinal trauma and hemorrhagic or ischemic stroke. Hypothermia has also been found to be advantageous as a treatment to protect both neural tissue and cardiac muscle tissue after a myocardial infract (MI). Again, the exact mechanism of benefit is not known, but inducing hypothermia in such situations, after the initial ischemic insult, may lessen damage by decreasing reperfusion injury, interrupting various chemical cascades that would otherwise damage the cells involved, protecting membrane integrity and perhaps even preventing certain genetic changes leading to apoptosis. Intentionally inducing hypothermia has generally been attempted by either surface cooling or by-pass pumping. Surface cooling has generally proved to be unacceptably slow, since the body heat to be removed must be transmitted from the core to the surface, and has sometimes been altogether unsuccessful since the body's thermoregulatory mechanisms act to oppose any attempt to induce hypothermia and generally succeed in preventing surface cooling from reducing the core temperature of the body. For example, the vasoconstriction and AV shunting may prevent heat generated in the core from being transmitted to the surface by the blood. Thus the surface cooling may only succeed in removing heat from the skin and surface tissue and thus cooling the surface, and not succeed in reducing the core temperature of the patient.

Another thermoregulatory mechanism that may thwart attempts to reduce core temperature by surface cooling is shivering. There are numerous temperature sensors on the body's surface, and these may trigger the body to begin shivering. Shivering results in the generation of a significant amount of metabolic heat, as much as five times more than the resting body, and especially where vasoconstriction and AV shunting reduce blood to the surface of the body, surface cooling such as by a cooling blanket can only reduce the temperature of the patient very slowly, if at all. Even if the thermoregulatory mechanisms are disabled by anesthesia or other drugs, it has generally been found that the cooling by surface measures such as blankets is unacceptably slow for inducing hypothermia. If the patient has fever and thus an elevated set point temperature (the temperature which the body's thermoregulatory responses act to maintain), the patient may even shiver at a temperature above normothermia. In such situations, it has been found that surface cooling is often unable to reduce the patient's temperature even to normothermia. Furthermore, besides often being ineffective and generally being unacceptably slow, surface cooling lacks sufficient control over the target temperature of the patient, since the methods are inadequate to quickly adjust the patient's body temperature and therefore may result in overshoot or other uncontrolled body temperature problems that cannot be adequately managed.

Inducing hypothermia using by-pass techniques is generally effective, fast and controllable, but is also subject to the shortcomings of the by-pass method for adding heat to control accidental hypothermia; it requires a very invasive procedure in an operating room under full anesthesia, with intubation, expensive equipment and highly trained personnel. Even in the situation of open heart surgery or neurosurgery where the patient is in the operating suite and has highly skilled personnel in attendance anyway, the by-pass mechanism requires pumping the blood with a mechanical pump through external circuit, which is generally thought to be very destructive of the blood and is generally not maintained for very long, preferably four hours or less, and cooling cannot be begun before the patient's thorax is opened and a shunt surgically installed, itself a procedure that might induce some neurological ischemia, or continued, nor warming effected, after the patient's thorax is closed. Thus any advantage of pre-cooling before the patient is opened, or continued after or re-warmed after the patient is closed, is not attained by this method, and the patient is exposed to the undesirable effects of external pumping.

Cold breathing gases and cold infusions have generally not been used to induce hypothermia. Breathing cold gases is generally ineffective to induce hypothermia since the lungs are generally structured to be able to breathe very cold air without rapidly inducing hypothermia. Injection of cold infusate would generally be unacceptable as a method of inducing and maintaining hypothermia because infusing the large volume of liquid that would be necessary to induce and maintain hypothermia for a useful length of time would be unacceptable.

The previously mentioned heat exchanged catheter placed in the bloodstream of a patient overcomes many of these inadequacies of the other methods of combating accidental hypothermia, or intentionally inducing hypothermia. Particularly in view of the body's own thermoregulatory attempts to maintain normothermia, a very efficient heat exchange catheter is highly desirable.

Under certain conditions heat is generated within the body or heat is added from the environment in excess of the body's ability to dissipate heat, and a persons develops a condition of abnormally high body temperature, a condition known as hyperthermia. Examples of this condition may result from exposure to a hot and humid environment or surroundings, overexertion, or exposure to the sun while the body's thermoregulatory mechanisms are disabled by drugs or disease. Additionally, often as a result of injury or disease, a person may establish a set point temperature that is above the normal body temperature of about 37° C. a condition generally known as fever. In another condition, malignant hyperthermia, a condition not well understood, the body may fail to dissipate enough heat and the temperature of the body may spiral to dangerous levels without the body's normal mechanisms being effective to return the patient to normothermia.

Prolonged and severe hyperthermia may have serious and very negative effects. For example, a child with prolonged and high fever as a result of spinal meningitis might suffer permanent brain damage. In stroke, the presence of even a mild fever has been found to correlate with very negative outcome. In such cases, it may be very desirable to counteract the body's attempt to establish a higher temperature, and instead to maintain at temperature at or near normothermia. However, the unaided body is acting to maintain a temperature above 37° C. and the body's own thermoregulatory mechanisms, such as AV shunting and shivering may render surface cooling altogether ineffective in reestablishing normothermia. The advantages of an effective core cooling method are sorely needed in such situations.

As with hypothermia, counter-parts to simple methods for treating undesirable hyperthermia exist, such as cold water baths and cooling blankets, as well as more effective but complex and invasive means such as cooled breathing gases and blood cooled during by-pass. These, however, are subject to the limitations and complications as described above in connection with hypothermia. In addition, as is the case when attempting to induce hypothermia, the thermoregulatory responses of the body such as vasoconstriction, AV shunting and shivering, may act directly to combat the attempt to cool the patient and thereby defeat the effort to treat the hyperthermia. In order to achieve the reduction of accidental, diseased or malignant hyperthermia, a catheter with sufficient heat exchange effectiveness to override the body's thermoregulatory defenses is needed.

For various reasons, it may be desirable to induce and/or maintain hyperthermia. For example, certain cancer cells may be sensitive to temperature elevations, and thus it may be possible to destroy those cancerous cells by elevating a patient's temperature to a level that is toxic to the cancer cells but the rest of the body can tolerate. As another example, a high temperature may be toxic to certain viruses at a level that the rest of the body can tolerate. Raising the patient's temperature above that which the virus can tolerate but within a temperature range the body can tolerate would help to rid the body of the virus. A heat exchanger that can add heat to the bloodstream of a patient at a sufficient rate to maintain the patient in a state of hyperthermia would therefore be desirable.

Besides intentionally induced hypothermia or hyperthermia, it is sometimes desirable to control a patient's temperature to maintain a target temperature, sometimes but not always normothermia. For example, in a patient under general anesthesia during major surgery, the anesthesiologist may wish to control the patient's body temperature by directly adding or removing heat. In such a situation, the patient's normal thermoregulatory responses are reduced or eliminated by anesthesia, and the patient may lose an extraordinary amount of heat to the environment. The patient's unaided body may not generate sufficient heat to compensate for the heat lost and the patient's temperature may drift lower. The anesthesiologist may wish to control the temperature at normothermia, or may prefer to allow the patient to become somewhat hypothermic, but control the depth and duration of the hypothermia. A device and method for precisely controlling body temperature by efficiently adding or removing heat to control a patient's temperature would be very desirable.

In addition to controlling the patient's body temperature, fast and precise control of the adjustments to a patient's thermal condition is very important when a patient's temperature is being manipulated. When using heat transfer from the surface to the core of a patient as by the application of warming or cooling blankets, besides being slow and inefficient, the control of the patient's core temperature is very difficult, if not impossible. The temperature of the patient tends to "overshoot" the desired low temperature, a potentially catastrophic problem when reducing the core temperature of a patient, especially to moderate or sever levels. The body's own metabolic activity and thermoregulatory responses may make even gross adjustments of core temperature by surface cooling difficult, slow, or even impossible. Speedy and precise control is generally not possible by such methods at all.

Control of body temperature using by-pass techniques is generally fairly precise and relatively fast, especially if large volumes of blood are being pumped through the system very quickly. However, as was previously stated, this method is complex, expensive, invasive and it is this very pumping of large quantities of blood that may be seriously damaging to the patient, particularly if maintained for any significant period of time, for example four or more hours.

An efficient heat exchanger might make possible the manipulation of temperature of a select portion of a patient's body. Generally, the temperature throughout the body is relatively constant and generally does not vary significantly from one location to another. (One exception is the skin, which because of exposure to the environment may vary significantly in temperature. In fact, many of the thermoregulatory mechanisms discussed above depend on the ability of the skin to maintain a different temperature, generally a lower temperature, than the temperature of the core of the body.) The mammalian body generally functions most efficiently at normothermia. In some instances, however, regional hypothermia or hyperthermia (hypothermia or hyperthermia of only a part of the body while the rest of the body is at a different temperature, preferably normothermia) may be advantageous. For example, it could be advantageous to cool the head for purposes of neuroprotection of the brain or cool the heart to protect the myocardium from suffering infarction during or after ischemia, or heating a cancerous region to destroy cancerous cells, while maintaining the rest of the body at normal, healthy temperature so that the disadvantages of whole body hypothermia or hyperthermia would not occur. Additionally, where the entire body is cooled, shivering and other thermoregulatory mechanisms may act to counter attempts to cool the body, and if only a specific region were targeted for cooling, those mechanisms might be obviated or eliminated.

A heat exchanger in contact with body fluid, such as blood, which was directed to the target area, might alter the temperature of that region if the heat exchanger was efficient enough to cool the blood sufficiently to cool the tissue in question even if the body temperature, i.e. the initial temperature of the blood flowing past the heat exchange region was normothermic. A heat exchange catheter with a highly efficient heat exchange region would be required for such an application. Where the catheter is inserted percutaneously into the vasculature, it is also highly desirable to have as small an insertion profile as possible to allow as small a puncture as possible, yet allow maximum surface area of the heat exchange region in contact with the flowing blood. Such a catheter is the subject of this application.

For all the foregoing reasons, there is a need for a means to add or remove heat from the body of a patient in an effective and efficient manner, while avoiding the inadequacies of surface heat exchange and avoiding the dangers of internal methods including by-pass methods. There is the need for a means of rapidly, efficiently and controllably exchanging heat with the blood of a patient so the temperature of the patient or target tissue within the patient can be altered or controllably maintained at some target temperature.

Positioning a catheter centrally within the flowing bloodstream may be important for various reasons. Contact between a hot or cold heat exchange region and the walls of a body conduit such as a blood vessel may affect the tissue at the point of contact. In some applications, such as where the user seeks to tack the surface of a dissected vessel to the wall of the vessel, or to thermally treat or ablate the tissue in question, the contact between the balloon and the surrounding body structure is important, even critical. Where, however, the contact is undesirable, it would be advantageous to have a means to prevent the heat exchange region from resting against the vessel wall.

Where temperature control of the temperature of the blood is the goal, it is also advantageous to position the heat exchange region in the center of a flow of body fluid, for example in the center of the lumen of a blood vessel so that the blood flow would surround the entire balloon and no portion of the balloon surface would be sheltered from the flow and thus prevented from exchanging heat at the balloon surface with the body fluid. This would also help prevent blood to pool in areas of low flow or lack of flow, which has been shown to cause blood to clot.

It would be particularly advantageous if the heat exchange surface could be configured to maximize the surface area in contact with the blood while minimizing the obstruction to fluid flow within the vessel. This is desirable both because maximum flow is important for maximum heat exchange and because maximum flow will assure that there is adequate blood supply to tissue downstream of the heat exchange region. Thus the rate of the blood flow past the heat exchange region should be maximized at the same time that the surface area of the heat exchange region within the stream of flowing blood is maximized. A catheter that could achieve these seemingly contradictory goals would be highly desirable.

Additionally, where heat exchange is occurring between two flowing fluids, it is most efficient to have counter-current flow. That is, the flow of the heat exchange liquid is counter to the flow direction of the fluid with which it is exchanging heat. Since a heat exchange catheter might be inserted into blood vessels in various ways that would result in the natural blood flowing being different in different instances (i.e. proximal to distal, or distal to proximal) it would advantageous to have a catheter wherein the direction of the fluid flow in the portion of the balloon exposed to the flow of the body fluid could be adjusted to flow in either direction to permit the catheter could be inserted into the blood vessel in either direction, and the direction of the flow of the heat exchange fluid adjusted to flow counter to the flow in the vessel.

If the heat exchange catheter is to be inserted into the vasculature of a patient, it is very advantageous to have a small insertion profile, that is to say a diameter of the device at insertion that is as small as possible. This permits the insertion of the device through a small sheath, puncture, or incision. Yet the surface area of the heat exchange region should be maximized when the catheter is functioning to exchange heat with the blood. Once again, these goals seem contradictory, and a heat exchange catheter that could achieve both characteristics would be highly advantageous.

SUMMARY OF THE INVENTION

The present invention provides a heat exchange catheter having a heat exchange region that comprises a balloon having multiple lumens for circulation of a heat exchange medium and a method for accomplishing intravascular heat exchange by circulation of heat exchange medium from outside the body through a multi-lumen shaft and through a multi-lumen balloon having curvilinear (e.g., helical, twisted or other curved configuration) balloon elements such as balloon lobes in contact with a patient's blood.

Further in accordance with the invention, there is provided a heat exchange catheter having a heat exchange region that comprises at least one balloon having multiple lumens for circulation of a heat exchange medium and a method for accomplishing intravascular heat exchange by circulation of heat exchange medium from outside the body through a multi-lumen shaft and through a shaped multi-lumen balloon in contact with a patient's blood. The method further may include altering the temperature of the heat exchange fluid outside the body so that it is a temperature different than the temperature of the patient's blood, placing the heat exchange region in contact with the patient's blood, and circulating the heat exchange fluid through the heat exchange region to exchange heat with the bloodstream at a sufficient rate and for a sufficient length of time to effect regional or whole body temperature modification of the patient.

Further in accordance with the invention, a heat exchange catheter of the invention may comprise a flexible catheter body or shaft having a proximal end and a distal end, the distal end of such catheter shaft being adapted to be inserted percutaneously into the vasculature or body cavity of a mammalian patient. A heat exchange region is provided on the catheter shaft, comprising a balloon with a plurality of lumens helically wound around a central axis. (A balloon is defined as a structure that is readily expandable under pressure and collapsible under vacuum and includes both elastomeric structures and non-elastomeric structures that are deformable in the manner described.) The shaft of the catheter preferably includes a fluid circulation path or lumen, and each heat exchange element preferably is attached at both ends of the shaft and incorporates a fluid circulation path or lumen that is in fluid communication with the fluid circulation path or lumen of the catheter shaft. In this manner, heat exchange fluid may be circulated into or through the heat exchange region as it is circumferentially surrounded by the body fluid.

Further in accordance with some embodiments of the invention, the heat exchange region may be less than the length of the portion of the catheter inserted into the patient and may be located at or near the distal end thereof. In such embodiments, an insulating region may be formed on the catheter shaft proximal to the heat exchange region to reduce unwanted transfer of heat to and from the proximal portion of the catheter shaft.

Further in accordance with the present invention, there is provided a system for heat exchange with a body fluid, the system including a) a liquid heat exchange medium and b) a heat exchange catheter having a heat exchange region comprising a balloon having helicaly formed lumens. The catheter includes a shaft having a proximal end and a distal end, the distal end adapted to be inserted percutaneously into a body cavity. The shaft having a circulation pathway therein for the circulation of heat exchange medium therethrough. The heat exchange region is attached to the catheter so that when the catheter is inserted in the body cavity, body fluid surrounds the heat exchange region.

Further in accordance with the present invention, the heat exchange region is deflated for percutaneous insertion into the patient's vasculature to a small diameter, and once positioned with the heat exchanger in the vasculature, the heat exchange region may be inflated to a larger diameter to increase the surface area of the heat exchange region for maximum heat exchange with the blood.

The system further may include a sensor or sensors attached to the patient to provide feedback on the condition of the patient, for example the patient's temperature. The sensors are desirably in communication with a controller that controls the heat exchange catheter based on the feedback from the sensors.

Still further in accordance with the present invention, there is provided a method for exchanging heat with a body fluid of a mammal. The method includes the steps of a) providing a catheter that has a circulatory fluid flow path therein and a heat exchange region thereon, such heat exchange region including heat exchange elements that are attached to the catheter shaft at the heat exchange region, b) inserting the catheter into a body cavity and into contact with a body fluid, the heat exchange elements thus being surrounded by the body fluid and c) causing a heat exchange medium to flow through the circulatory flow path of the catheter so that the medium exchanges heat with a body fluid through the heat exchange elements. Each of the heat exchange elements may be hollow balloon lobes, and step C of the method may include causing heat exchange fluid to flow through the hollow heat exchange elements.

It is an object of this invention to provide an effective and advantageous heat exchange region for adding heat to a patient suffering from hypothermia.

It is a further object of this invention to provide an effective means for removing heat from the bloodstream of a patient suffering from hyperthermia.

It is a further object of this invention to provide an effective means of adding or removing heat from a patient to induce normothermia.

It is a further object of this invention to provide an effective means for maintaining normothermia.

It is a further object of this invention to provide an effective means of cooling a patient to a target temperature and controllably maintaining that temperature.

It is a further object of this invention to provide a heat exchange catheter that has an advantageous configuration that provides for maximum heat exchange with blood flowing in heat exchange proximity to the heat exchange region.

It is a further object of this invention to provide a heat exchange catheter that has an advantageous shape that attains an advantageous ratio of heat exchange surface area while maintaining adequate flow in a blood vessel.

It is a further object of this invention to provide a catheter with a sufficiently effective and efficient heat exchange region to cool a target region of a patient.

It is a further object of this invention to provide a catheter with a sufficiently effective and efficient heat exchange region to precisely maintain a patient at a target temperature.

It is a further object of this invention to provide a heat exchange catheter that is configured to efficiently exchange heat with the blood of a patient while allowing continued flow of the blood past the catheter with a minimum of restriction to that blood flow.

It is a further object of this invention to provide a heat exchange catheter having a heat exchange region comprised of multiple balloon elements such as lobes.

It is a further object of this invention to provide a heat exchange catheter having an insulated shaft.

It is a further object of this invention to provide an effective method of controlling the temperature of a body fluid.

It is a further object of this invention to provide an effective method of warming a body fluid.

It is a further object of this invention to provide an effective method of cooling a body fluid.

It is a further object of this invention to provide an effective method for inducing hypothermia.

It is a further object of this invention to provide a catheter having a heat exchange region wherein the temperature is controlled by the temperature of flowing heat exchange fluid and wherein the direction of the fluid flow may be reversed.

It is a further object of this invention to provide a heat exchange catheter having a heat exchange region wherein, when the heat exchange region is placed within a blood vessel, the shape of the heat exchange region assists in centering the heat exchange region within the vessel.

It is a further object of this invention to provide a heat exchange catheter having a heat exchange region composed of multiple, non-coaxial balloon elements such as lobes of a multi-lobed balloon.

These and other objects of this invention will be understood with reference to the following drawings and description.

BRIEF DESCRIPTION OF THE DRAWINGS

FIG. 1 is a perspective drawing of an embodiment of the catheter of the invention.

FIG. 1A is a perspective drawing of an alternative tie-down at the proximal end of the catheter shown in FIG. 1.

FIG. 2 is a cross-sectional drawing of the shaft of the catheter taken along the line 2-2 in FIG. 1.

FIG. 3 is a cross-sectional drawing of the heat exchange region of the catheter taken along the line 3-3 in FIG. 1.

FIG. 3A is a cross-sectional drawing of the heat exchange region of the catheter taken along the line 3A-3A in FIG. 1.

FIG. 4 is a perspective drawing of a segment of the heat exchange region of the catheter within the circle 4-4 in FIG. 1.

FIG. 5 is a cross-sectional drawing of the heat exchange region of the catheter taken along the line 5-5 in FIG. 1.

FIG. 6 is a perspective drawing of a segment of the heat exchange region of the catheter within the circle 6-6 in FIG. 1.

FIG. 7 is a perspective drawing of the multi-lobed balloon of one embodiment of the invention.

FIG. 8 is a perspective drawing of the distal portion of the shaft of one embodiment of the invention.

FIG. 9 is a perspective drawing, partially in ghost, of the heat exchange region formed by the shaft and multi-lobed balloon of FIGS. 7 and 8.

FIG. 10 is an expanded view of the attachment of the central lumen of the balloon to the shaft of the catheter of FIG. 9 showing the region within the circle 10-10 in FIG. 9.

FIG. 10A is an expanded view of the plug between the shaft and the central lumen of the balloon of the catheter of FIG. 9 showing the region within the circle 10A-10A in FIG. 9.

FIG. 12 is a sectional view of the proximal portion of the heat exchange region of one embodiment of the invention.

FIG. 12A is a cross-sectional view of a portion of the heat exchange region taken along the line 12A-12A of FIG. 12.

FIG. 12B is a cross-sectional view of a portion of the heat exchange region taken along the line 12B-12B of FIG. 12.

FIG. 12C is a cross-sectional view of a portion of the heat exchange region taken along the line 12C-12C of FIG. 12.

FIG. 13 is a sectional view of the distal portion of the heat exchange region of one embodiment of the invention.

FIG. 13A is a cross-sectional view of a portion of the heat exchange region taken along the line 13A-13A of FIG. 13.

FIG. 13B is a cross-sectional view of a portion of the heat exchange region taken along the line 13B-13B of FIG. 13.

FIG. 14 is a sectional view of the distal portion of the heat exchange region of one embodiment of the invention.

FIG. 15B is a cross-section taken along the line 15B-15B in FIG. 15A.

FIG. 15C is a cross-section taken along the line 15C-15C in FIG. 15A.

FIG. 15D is a cross-section taken along the line 15D-15D in FIG. 15A.

FIG. 15E is a cross-section taken along the line 15E-15E in FIG. 15A.

FIG. 15F is a cross-section taken along the line 15F-15F in FIG. 15A.

FIG. 16A is a perspective view of one embodiment of an intravascular heat exchange catheter according to the present invention.

FIG. 16B is a front perspective view of one embodiment of an extracorporeal temperature control console that is useable in conjunction with the catheter of FIG. 16A to accomplish temperature management of a human or veterinary patient.

FIG. 17 is a flowchart of an exemplary method of the invention.

DETAILED DESCRIPTION

Figure 11:
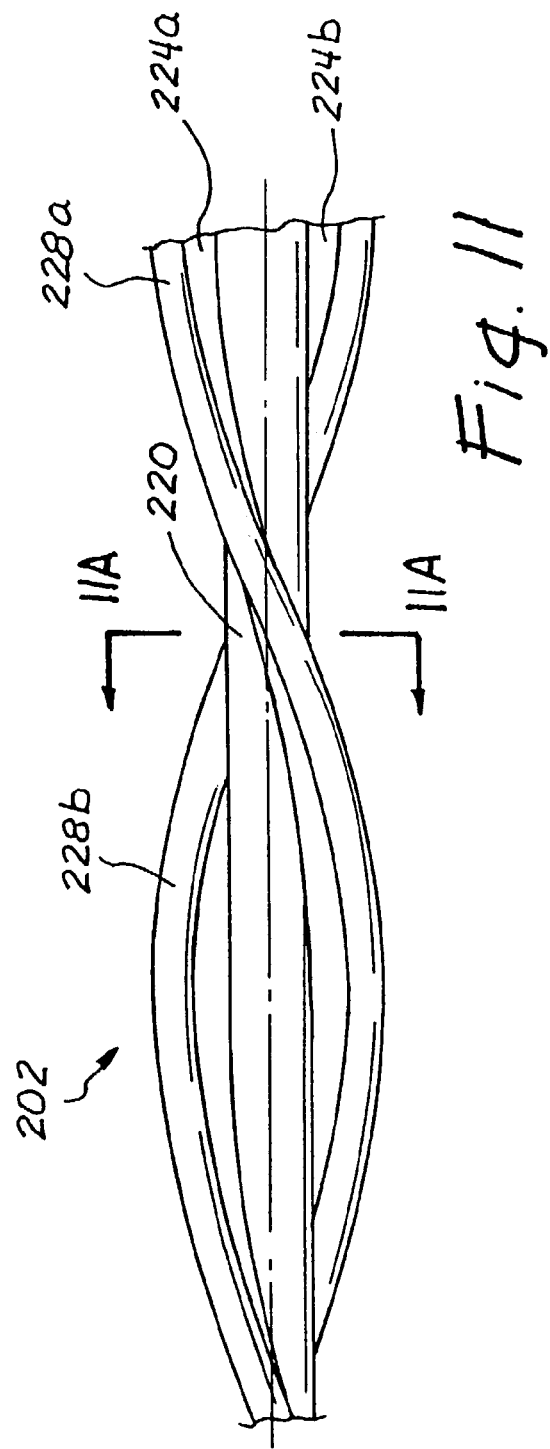
FIG. 11 is a perspective view of a portion of a multi-lobed curvilinear heat exchange balloon of one embodiment of the invention.

The present invention provides an improved heat exchange catheter that provides an efficient and effective heat exchange region to exchange heat with body fluid while maintaining a minimum insertion profile of the catheter. The heat exchange catheter generally comprises a catheter having a shaft for the flow of heat exchange fluid to and from a heat exchange region, and the heat exchange region comprising an advantageously configured multiple lumen balloon wherein the heat exchange fluid flows through the balloon and blood flows over the outside of the balloon and heat is exchanged through the walls of the balloon between the heat exchange fluid flowing inside the balloon and the blood flowing outside the balloon.

Referring to FIGS. 1 through 10A, in one advantageous embodiment, the catheter is comprised of a shaft 50 with a heat exchange region 100 thereon. The shaft has two roughly parallel lumens running through the proximal shaft, an inflow lumen 52 and an outflow lumen 54. The shaft generally also comprises a working lumen 56 running therethrough for the insertion of a guide wire, or the application of drugs, radiographic dye, or the like to the distal end of the catheter. The heat exchange region comprises a four-lumen balloon, with three outer lumens 58, 60, 62 disposed around an inner lumen 64 in a helical pattern. In the particular embodiment shown, the balloon preferable makes one full rotation about the inner lumen 64 for each 2 to 4 inches of length. All four lumens are thin walled balloons and each outer lumen shares a common thin wall segment 66, 68, 70 with the inner lumen. The balloon is approximately twenty-five centimeters long, and when inflated has an outer circumference 72 of approximately 0.328 in. When deflated, the profile is generally less than about 9 French (3 French is 1 mm in diameter). When the balloon portion is installed on the shaft, both the balloon proximal end 74 and the distal end 76 are sealed around the shaft in a fluid tight seal as will be described below.

The catheter is attached at its proximal end to a hub 78. At the hub, the guide wire lumen 56 communicates with a guide wire port 80, the inflow lumen 52 is in fluid communication with an inflow port 82, and the outflow lumen 54 is in communication with an outflow port 84. Attached at the hub and surrounding the proximal shaft is a length of strain relief tubing 86 which may be, for example, a length of heat shrink tubing. The strain relief tubing may be provided with suture tie downs 88, 90. Alternatively, a butterfly tie-down 92 may be provided. (See FIG. 1A). Between the strain relief tubing 86 and the proximal end of the balloon 74, the shaft 50 is extruded with an outer diameter of about 0.118 inches. The internal configuration is as shown in cross-section in FIG. 2. Immediately proximal of the balloon attachment 74, the shaft is necked down 94. The outer diameter of the shaft is reduced to about 0.100 to 0.110 inches, but the internal configuration with the three lumens is maintained. Compare, for example, the shaft cross-section of FIG. 2 with the cross-section of the shaft shown in FIG. 3. This length of reduced diameter shaft remains at approximately constant diameter of about 0.100 to 0.110 inches between the necked down location at 94 and the distal location 96 where the outflow lumen is sealed and the guide wire extension tube 98 is attached as will be described.

At the necked down location 94, a proximal balloon marker band 102 is attached around the shaft. The marker band is a radiopaque material such as a platinum or gold band or radiopaque paint, and is useful for locating the proximal end of the balloon by means of fluoroscopy while the catheter is within the body of the patient.

At the marker band, all four lobes of the balloon are reduced down and fastened to the shaft 50. This may be accomplished by folding the outer lobes of the balloon 58, 60, 62 down around the inner lumen 64, placing a sleeve, for example a short length of tubing, over the balloon and inserting adhesive, for example by wicking the adhesive, around the entire inner circumference of the sleeve. The inner lumen is then fastened to the shaft using a second short length of tubing. A short length for example 1 mm, of intermediate tubing 104 is heat welded to the inside of the inner lumen. The intermediate tube has an outer diameter approximately the same as the inner diameter of the inner lumen. The intermediate tube is then slid over the shaft at about the location of the neck-down near the proximal marker 102 and adhesive 106 is wicked into the space between the inside of the intermediate tubing and the outer surface of the shaft 50.

A similar process may be used to attach the distal end of the balloon. The distal end of the balloon is attached down around the guide wire extension tube 98 rather than the shaft, but otherwise the attachment is essentially similar.

Distal of the proximal balloon seal, under the balloon, an elongated window 108 cut through the wall of the outflow lumen in the shaft. Along the proximal portion of the balloon, five slits, e.g. 110, are cut into the common wall between each of the outer lumens 58, 60, 62 and the inner lumen 64. Because the outer lumens are twined about the inner lumen in a helical fashion, each of the outer tubes passes over the outflow lumen of the inner shaft member at a slightly different location along the length of the inner shaft, and therefore an elongated window 108 is cut into the outflow lumen of the shaft so that each outer lumen has at least one slit e.g. 110 that is located over the window in the shaft. Additionally, there is sufficient clearance between the outer surface of the shaft and the wall of the inner lumen to create sufficient space to allow relatively unrestricted flow through heat exchange fluid through all 5 slits in each outer lumen, around the shaft, and through the elongate window 108 into the outflow lumen 54 in the shaft 50.

Distal of the elongated window in the outflow lumen, the inner member 64 of the four-lumen balloon is sealed around the shaft in a fluid tight plug. Referring to FIG. 10*a*, the plug is formed by, for example shrinking a relatively thick length of PET tubing to form a length of plug tubing 112 where the inner diameter of the length of plug tubing is approximately the same as the outer diameter of the shaft at the location where the plug is to be formed. The plug tubing is slid over the shaft and fits snugly against the shaft. The shaft is generally formed of a material that is not heat shrinkable. As may be seen in FIG. 10A and FIG. 3, some clearance exists between the outer wall of the shaft and the inner wall of the inner lumen 64. The walls of the inner lumen are composed of thin heat shrinkable material, for example PET. A probe with a resistance heater on the distal end of the probe is inserted into the guide wire lumen of the shaft and located with the heater under the plug tubing. The probe is heated, causing the heat shrink wall of the inner lumen to shrink down against the plug tubing, and the plug tubing to shrink slightly down against the shaft. The resultant mechanical fit is sufficiently fluid tight to prevent the outflow lumen and the space between the shaft and the wall of the inner lumen from being in fluid communication directly with the inner member or the inflow lumen except through the outer lumens as will be detailed below.

Just distal of the plug, the outflow lumen is closed by means of heat sealing 99, and the inflow lumen is skived open to the inner member 101. This may be accomplished by necking down the shaft at 96, attaching a guide wire extension tube 98 to the guide wire lumen, and at the same location opening the inflow lumen to the interior of the inner lumen and heat sealing the outflow lumen shut. The guide wire extension tube continues to the distal end of the catheter 114 and thereby creates communication between the guide wire port 80 and the vessel distal of the catheter for using a guide wire to place the catheter or for infusing drugs, radiographic dye, or the like beyond the distal end of the catheter.

The distal end of the balloon 76 is sealed around the guide wire extension tube in essentially the same manner as the proximal end 74 is sealed down around the shaft. Just proximal of the distal seal, five slits 116 are cut into the common wall between each of the three outer lumens 58, 60 62 of the balloon and the inner lumen 64 so that each of the outer lumens is in fluid communication with the inner lumen.

Just distal of the balloon, near the distal seal, a distal marker band 118 is placed around the guide wire extension tube. A flexible length of tube 120 may be joined onto the distal end of the guide wire tube to provide a soft tip to the catheter as a whole.

In use, the catheter is inserted into the body of a patient so that the balloon is within a blood vessel, for example in the inferior vena cava (IVC). Heat exchange fluid is circulated into the inflow port 82, travels down the inflow lumen 52 and into the inner lumen 64 distal of the plug tube 112. The heat exchange fluid travels down the inner lumen, thence through slits 116 between the inner lumen 64 and the three outer lumens 58, 60, 62.

The heat exchange fluid then travels back through the three outer lumens of the balloon to the proximal end of the balloon. A window 108 is cut in the outflow lumen of the shaft proximal of the plug 99. in the distal portion of the balloon, approximately above the window, about five slits 110 are cut in the wall between each of the outer balloon lumens 58, 60, 62 and the inner lumen 64. Since the outer lumens are wound in helical pattern around the inner lumen, at some point at least one of the slits from each of the outer lumens is located directly over the window 108 in the outflow lumen. Additionally, there is sufficient clearance between the wall of the inner lumen and the shaft, as illustrated at 102 in FIG. 10A, that even if the slits are not directly over the window 108, flow into the space between the wall of the inner lumen and the outer wall of the shaft 50 allows the fluid to flow ultimately into the window 108 and out the outflow lumen without undue resistance. It then flows out the outflow lumen and out of the catheter through the outflow port 84. The fluid may be pumped at a pressure of, for example, 40-50 pounds per square inch (psi), and at a pressure of about 41 psi, a flow of as much as 500 milliliters per minute may be achieved.

Counter-current circulation between the blood and the heat exchange fluid is highly desirable for efficient heat exchange between the blood and the heat exchange fluid. Thus if the balloon is positioned in a vessel where the blood flow is in the direction from proximal toward the distal end of the catheter, for example if it were placed from the femoral vein into the ascending vena cava, it is desirable to have the heat exchange fluid in the outer balloon lumens flowing in the direction from the distal end toward the proximal end of the catheter. This is achieved by the arrangement described above. It is to be readily appreciated, however, that if the balloon were placed so that the blood was flowing along the catheter in the direction from distal to proximal, for example if the catheter was placed into the IVC from a jugular insertion, it would be desirable to have the heat exchange fluid circulate in the outer balloon lumens from the proximal end to the distal end. Although in the construction shown this is not optimal and would result is somewhat less effective circulation; this could be accomplished by reversing which port is used for inflow direction and which for outflow.

Where heat exchange fluid is circulated through the balloon that is colder than the blood in the vessel into which the balloon is located, heat will be exchanged between the blood and the heat exchange fluid through the outer walls of the outer lumens, so that heat is absorbed from the blood. If the temperature difference between the blood and the heat exchange fluid (sometimes called $\Delta T$), for example if the blood of the patient is about 37° C. and the temperature of the heat exchange fluid is about 0° C., and if the walls of the outer lumens conduct sufficient heat, for example if they are thin (0.002 inches or less) of a plastic material such as polyethylene terephthalate (PET), enough heat may be exchanged (for example about 200 watts) to lower the entire body temperature of the patient at a useful rate, for example 3-6° C. per hour.

The helical structure of the outer lumens has the advantage over straight lumens of providing greater length of heat exchange fluid path for each length of the heat exchange region. It may also provide for enhanced flow patterns for heat exchange between flowing liquids. Additionally, the helical shape may assist in maintaining flow in a roughly tubular conduit, for example blood flow in a blood vessel, by not creating a firm seal around the heat exchange region since the exterior of the heat exchange region is not tubular.

The fact that the heat exchange region is in the form of an inflatable balloon also allows for a minimal insertion profile, for example 9 French or less, while the heat exchange region may be inflated once inside the vessel for dramatically increased functional diameter of the heat exchange region in operation. After use, the balloon can be collapsed for easy withdrawal.

Such a configuration is adequately efficient in heat exchange, the use of a system which controls the temperature of the heat exchange fluid which system is directed in response to signals representing the temperature of a patient is adequate to exercise control over the body temperature of a patient.

Figure 11A:
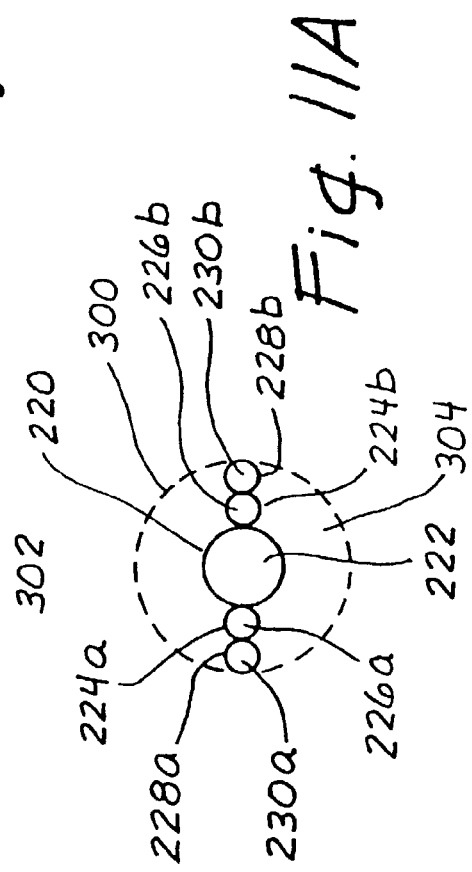
FIG. 11A is a cross sectional view of the heat exchange region taken along the line 11A-11A in FIG. 11.
Figure 15A:
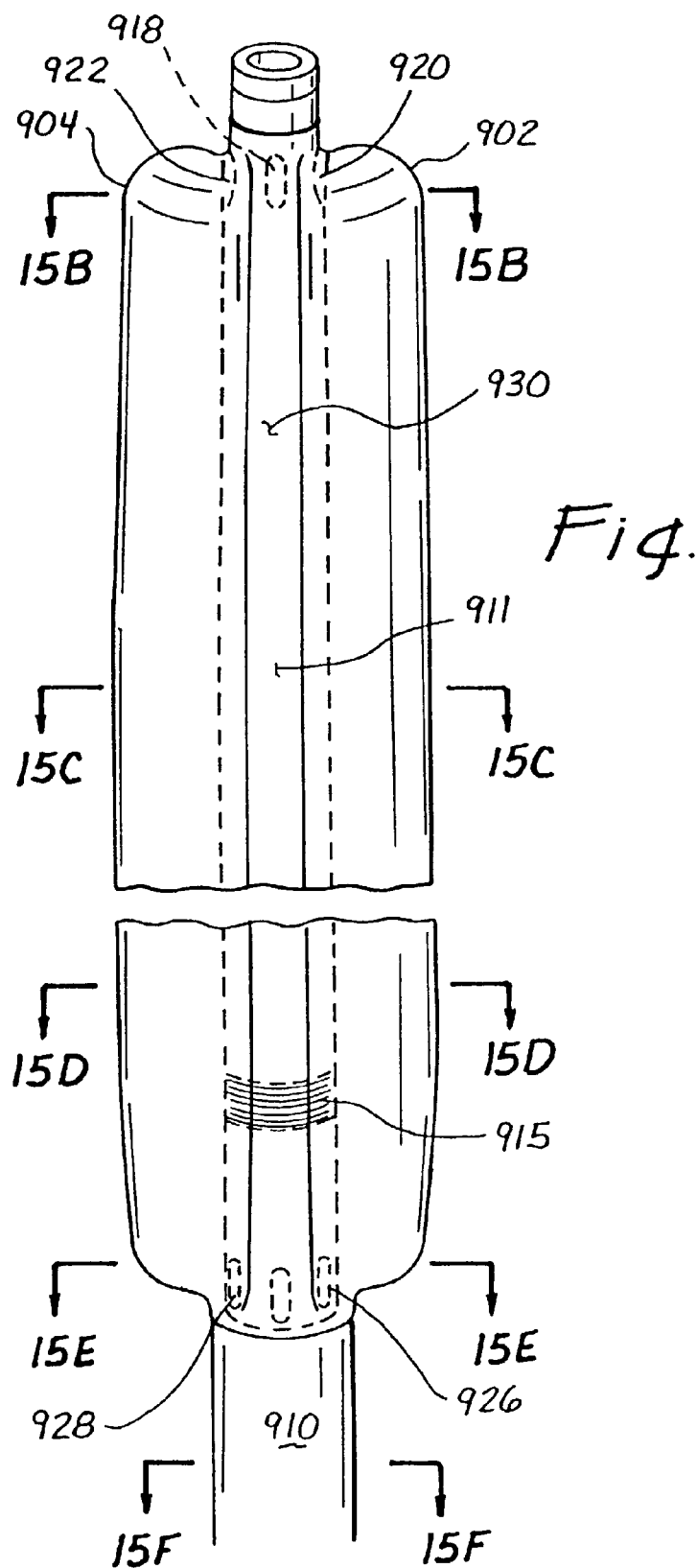
FIG. 15A is a side view, partially in ghost, of the heat exchange region of one embodiment of the invention.

Referring now to FIGS. 11 through 13B, in another example of a preferred embodiment, the heat exchange region is in the form that may be called a twisted ribbon. The heat transfer fluid circulates to and from the heat exchange region 202 via channels formed in the shaft 206 in much the same manner as previously described for shaft 50. FIGS. 11 and 11A illustrate this embodiment of a heat exchange region 202 comprising a plurality of balloon elements in the form of tubular members that are stacked in a helical plane. More specifically, a central tube 220 defines a central lumen 222 therewithin. A pair of smaller intermediate tubes 224*a*, 224*b* attaches to the exterior of the central tube 220 at diametrically opposed locations. As illustrated here, the tubes are attached or alternatively extruded in a unitary extrusion so that the balloon elements form essentially the lobes of a multi-lobed balloon. Each of the smaller tubes 224*a*, 224*b* defines a fluid lumen 226*a*, 226*b* therewithin. A pair of outer tubes 228*a*, 228*b* attaches to the exterior of the intermediate tubes 224*a*, 224*b* in alignment with the aligned axes of the central tube 220 and intermediate tubes 224*a*, 224*b*. Each of the outer tubes 228*a*, 228*b* defines a fluid lumen 230*a*, 230*b* within. By twisting the intermediate and outer tubes 224*a*, 224*b*, 228*a*, 228*b* around the central tube 220, the helical ribbon-like configuration of FIG. 11 is formed.

An inflow path of heat exchange medium is provided by the central tube 220, as described in greater detail below. The intermediate tubes 224*a*, 224*b* and outer tubes 228*a*, 228*b* define a fluid outflow path within the heat exchange region 202. Heat exchange fluid is transferred into the catheter through an inflow port of a hub at the proximal end of the shaft and after circulation is removed via an outflow port in essentially the same manner as previously described. Likewise, a guide wire port is provided on the hub.

Now with reference to FIGS. 12 and 12A-12C, a proximal manifold of the heat exchange region 202 will be described. The shaft 206 extends a short distance, desirably about 3 cm, within the central tube 220 and is thermally or adhesively sealed to the interior wall of the central tube as seen at 250. As seen in FIG. 12A, the shaft 206 includes a planar bulkhead 252 that generally evenly divides the interior space of the shaft 206 into an inflow lumen 254 and an outflow lumen 256. A working or guide wire lumen 260 is defined within a guide wire tube 262 that is located on one side of the shaft 206 in line with the bulkhead 252. Desirably, the shaft 206 is formed by extrusion.

The outflow lumen 256 is sealed by a plug 264 or other similar expedient at the terminal end of the shaft 206 within the central tube 220. The inflow lumen 254 remains open to the central lumen 222 of heat exchange region 202. The guide wire tube 262 continues a short distance and is heat bonded at 270 to a guide wire extension tube 272 generally centered within the central tube 220.

A fluid circulation path is illustrated by arrows in FIG. 12 and generally comprises fluid passing distally through the inflow lumen 254 and then through the entirety of the central lumen 222. Fluid returns through the lumens 226*a*, 226*b*, and 230*a*, 230*b* of the intermediate and outer tubes 224*a*, 224*b*, and 228*a*, 228*b*, respectively, and enters reservoirs 274 and 275. These reservoirs are in fluid communication with each other, forming essentially one terminal reservoir in fluid communication with one window 276 in the outflow lumen. Alternatively, two windows may be formed 276 and a counterpart not shown in FIG. 12 one helical twist farther down the shaft, between each side of the twisted ribbon (i.e., lumens 224*a* and 224*b* on one side, and 228*a* and 228*b* on the other side). In this way, one reservoir from each side of the twisted ribbon is formed in fluid communication with the outflow lumen 256, each through its own window (configuration not shown). Fluid then enters the outflow lumen 256 through apertures, e.g., 276, provided in the central tube 220 and a longitudinal port 278 formed in the wall of the shaft.

A distal manifold of the heat exchange region 202 is shown and described with respect to FIGS. 13 and 13A-13B. The outer tubes 228a, 228b taper down to meet and seal against the central tube 220 which, in turn, tapers down and seals against the guide wire extension tube 272. Fluid flowing distally through the central lumen 222 passes radially outward through a plurality of apertures 280 provided in the central tube 220. The apertures 280 open to a distal reservoir 282 in fluid communication with lumens 226a, 226b, and a distal reservoir 281 in fluid communication with lumens 230a, 230b of the intermediate and outer tubes 224a, 224b, and 228a, 228b.

With this construction, heat exchange fluid introduced into the input port 240 will circulates through the inflow lumen 254, into the central lumen 222, out through the apertures 280, and into the distal reservoir 282. From there, the heat exchange fluid will travel proximally through both intermediate lumens 226a, 226b and outer lumens 230a, 230b to the proximal reservoirs 274 and 275. Fluid then passes radially inwardly through the apertures 276 and port 278 into the outflow lumen 256. Then the fluid circulates back down the shaft 206 and out the outlet port.

The twisted ribbon configuration of FIGS. 11-13C is advantageous for several reasons. First, the relatively flat ribbon does not take up a significant cross-sectional area of a vessel into which it is inserted. The twisted configuration further prevents blockage of flow through the vessel when the heat exchange region 202 is in place. The helical configuration of the tubes 224a, 224b, 228a, 228b also aids to center the heat exchange region 202 within a vessel by preventing the heat exchange region from lying flat against the wall of the vessel along any significant length of the vessel. This maximizes heat exchange between the lumens and the blood flowing next to the tubes. It also helps prevent thermal injury to the vessel wall by avoiding prolonged contact between a specific location on the vessel wall and the heat exchange region of the catheter. Because of these features, the twisted ribbon configuration is ideal for maximum heat exchange and blood flow in a relatively small vessel such as the carotid artery. As seen in FIG. 11A, an exemplary cross-section has a maximum functional diameter 300 of about 5 mm, permitting treatment of relatively small vessels.

The deflated profile of the heat exchange region is small enough to make an advantageous insertion profile, as small as 7 French for some applications. Even with this low insertion profile, the heat exchange region is efficient enough to adequately exchange heat with blood flowing past the heat exchange region to alter the temperature of the blood and affect the temperature of tissue downstream of the heat exchange region. Because of its smaller profile, it is possible to affect the temperature of blood in smaller vessels and thereby provide treatment to more localized body areas.

This configuration has a further advantage when the heat exchange region is placed in a tubular conduit such as a blood vessel, especially where the diameter of the vessel is approximately that of the major axis (width) of the cross section of the heat exchange region. The configuration tends to cause the heat exchange region to center itself in the middle of the vessel. This creates two roughly semicircular flow channels within the vessel, with the blood flow channels divided by the relatively flat ribbon configuration of the heat exchange region. It has been found that the means for providing maximum surface for heat exchange while creating minimum restriction to flow is this configuration, a relatively flat heat exchange surface that retains two approximately equal semicircular cross-sections. This can be seen in reference to FIG. 11A if the essential functional diameter of the dashed circle 300 is essentially the same as a vessel into which the twisted ribbon is placed. Two roughly semi-circular flow paths 302, 304 are defined by the relatively flat ribbon configuration of the heat exchange region, i.e. the width or major axis (from the outer edge of 228a to the outer edge of 228b) is at least two times longer than the height, or minor axis (in this example, the diameter of the inner tube 222) of the overall configuration of the heat exchange region. It has been found that if the heat exchange region occupies no more than about 50% of the overall cross-sectional area of the circular conduit, a highly advantageous arrangement of heat exchange to flow is created. The semi-circular configuration of the cross-section of the flow channels is advantageous in that, relative to a round cross-sectioned heat exchange region (as would result from, for example, a sausage shaped heat exchange region) the flow channels created minimize the surface to fluid interface in a way that minimizes the creation of laminar flow and maximizes mixing.

Maximum blood flow is important for two reasons. The first is that maximum flow downstream to the tissue is important, especially if there is obstruction in the blood flow to the tissue, as would be the case in ischemic stroke or an MI. The second reason is that heat exchange is highly dependent on the rate of blood flow past the heat exchange region, with the maximum heat exchange occurring with maximum blood flow, so maximum blood flow is important to maximizing heat transfer.

A third exemplary embodiment is very similar to the twisted ribbon embodiment just described, except that the outermost tubes 230a', 230b' are shorter than the intermediate tubes 226a', 226b', and terminate short of the intermediate tubes, and therefore the heat exchange region has a staggered diameter. Such a construction is illustrated in FIG. 14. The configuration of the shaft and the proximal portion of the balloon are essentially the same as the twisted ribbon catheter just described. However, on the distal end of the heat exchange region, the central lumen 220' is manifolded to the intermediate lumens 226a' and 226b' by slits, for example 280'. The outer lumens 230a' and 230b', however, do not extend all the way to the distal location where the intermediate tubes are manifolded to the central lumen. Instead, at a location proximal of the distal end of the intermediate tube, the wall between the outer lumens and the intermediate lumens are cut 295' so that the outer and intermediate lumens are manifolded to be in fluid communication with each other. In this way, heat exchange fluid may be introduced into the inflow port, flow down the inflow lumen to the central lumen, exit the central lumen through slits into the intermediate lumen. The heat exchange fluid then travels proximately down the intermediate lumen for some distance to the point where the outer lumens are in fluid communication with the intermediate lumens through slits 295'. The heat exchange fluid travels proximally down both the intermediate lumen and the outer lumen to the proximal manifold, which is essentially the same as described in the previous embodiment and illustrated in FIG. 12. According to this construction, a very small diameter heat exchange region can be placed very distal in a small vessel, and yet a larger diameter heat exchange region be located proximally in a larger vessel or a larger diameter portion of the vessel into which the distal portion of the staggered diameter heat exchange region is located. The lengths of the various lumens illustrated in FIG. 14 is not meant to be literal, and it will readily be appreciated that the lengths and diameters of the lumens may be adjusted to achieve the configuration that may be desired for various applications. In some applications as will be readily appreciated by those of skill in the art, more than merely two lumens may be similarly stacked to achieve a configuration with one, two, three or even more steps in diameter of the heat exchange region.

In any configuration, for maximum heat exchange results, it is important that the difference in temperature between the blood and heat exchange region be as large as possible. Because of the long length of catheter required for selective cooling of the brain within the carotid artery in conjunction with femoral insertion, maximum thermal insulation of the shaft is important to maximize heat transfer with the blood flowing to the brain and minimize heat transfer with the blood flowing away from the brain. In use, the catheter is generally passed through a vessel of relatively large diameter, for example the Vena Cava or the abdominal aorta, so that there is room within the vessel around the proximal shaft to utilize an inflatable insulating region around the shaft. Such an inflatable region is more fully described in parent application Ser. No. 09/489,142 filed Jan. 21, 2000, titled Heat Exchange Catheter with Improved Insulated Region, of which this application is a Continuation in Part and which has previously been incorporated in full by reference. Because the insulating region 204 is deflated at insertion, and inflated thereafter, the incision or puncture into the vasculature is minimized but once inflated, the insulation is maximized. The insulation region is, of course, deflated for removal.

An alternative construction to the heat exchange balloon is illustrated in FIGS. 15A through 15F wherein the heat exchange region is formed of a four lobed balloon, the balloon having three collapsible outer balloon lobes 902, 904, 906 located in roughly linear and parallel configuration around a central collapsible lumen 908. The catheter has a proximal shaft 910 formed having two lumens running the length of the shaft, the first lumen forming an inlet channel 912 and the second lumen forming an outlet channel 914. The interior of the shaft is divided into the two lumens by webs 916, 917, but the lumens do not occupy equal portions of the interior of the shaft. The inlet channel occupies about ⅓ of the circumference of the interior; the outlet channel occupies about ⅔ of the circumference of the interior for reasons that will be explained below. A guide wire lumen 929 is formed running down the center of the shaft.

Within the proximal portion of the heat exchange region of the catheter, the shaft is affixed to the balloon. A transition region 915 is formed between the shaft 910 and the tube 911 forming the central collapsible lumen 908. The outlet channel is plugged 917, the tube 911 is affixed over the shaft 910 by, for example gluing, at the transition 915, and the shaft ends. A guide wire extension tube 930 is attached to the guide wire lumen 929 with the guide wire tube running to the distal end of the catheter. Alternatively, the outer wall of the shaft may be removed at the transition region, leaving only the tube which forms the guide wire lumen intact.

After the outlet lumen is plugged 917 and the shaft attached to the interior of the tube which forms the central lumen of the balloon, with the inlet channel open into the interior of the central lumen, as shown at FIG. 15C, the inlet channel occupies the entire inner lumen of the balloon 908 except for the guide wire extension tube 930.

At the distal end of the balloon, inlet orifices 918, 920, 922 are formed between the inlet channel and the three collapsible balloon outer lobes 902, 904, 906. At the proximal end of the heat exchange region, outlet orifices 924, 926, 928 are formed between the interior of each outer balloon lobe and the outlet channel 914 in the shaft. These may be formed by, for example, cutting or burning holes in the common wall between the central lumen and the outer balloon lobes and simultaneously through the wall of the shaft over the outlet lumen. As may be seen in FIG. 15D, the configuration of the outlet channel is such that the wall of the outlet channel occupies a sufficient circumference of the shaft, as noted above, that communication between the outlet channel and the interior of each of the three outer balloon lobes may be created.

As may be appreciated, in use, heat exchange fluid may be introduced into the inlet channel through an inlet port (not shown), and flow down the inlet channel in the shaft 912 and into the central lumen of the balloon 908. It then flows to the distal end of the heat exchange region, through the inlet orifices 918, 920, 922 in the common wall between the central lumen and the three outer balloon lobes and flows into the interior lumens of the balloon lobes 919, 921, 923, travels back down each of the three balloon lobes and re-enters the shaft through the outlet orifices 924, 926, 928. The heat exchange fluid then flows down the outlet channel 914 to the proximal end of the catheter. In this, way heat exchange fluid may be circulated through the three outer balloon lobes to add heat to the blood flowing in heat transfer proximity to the balloons if the heat exchange fluid is warmer than the blood, or to remove heat from the blood if the heat exchange fluid is cooler than the blood.

The balloon is formed from a material that will permit significant thermal exchange between the heat exchange fluid on the interior of the balloon and the body fluid flowing over the outside of the balloon in heat exchange proximity to the surface of the balloon. One such appropriate material is very thin plastic material such as PET, which may also be made strong enough to withstand the pressure necessary for adequate flow of the heat exchange fluid while at the same time being thin enough, perhaps less than 2 mils (0.002 inches).

It may also readily be appreciated that the same heat exchange balloons of the various types described herein may be used to add heat to the blood stream or remove heat from the blood stream depending on the relative temperature of the heat exchange fluid and the blood flowing in heat exchange proximity to the balloon. That is, the same device at the same location may be used alternately to add or to remove heat merely by controlling the temperature of the heat exchange fluid within the device. When attached to a control unit that can alter the temperature of the heat exchange fluid in response to an external signal, for example a sensed temperature of a patient in which the catheter has been placed, the device may be used to automatically control the temperature of the patient.

As previously described, precise control over a patient's temperature is highly desirable. Because the heat exchange regions of the catheters of this invention are highly efficient and are able to add or remove heat from a patient with great speed and effectiveness, very precise control over the temperature of a patient is possible. Precise control, for example with a precision of one or two tenths of a degree Celsius, is possible using a heat exchange catheter of this invention and a feedback control mechanism as illustrated in FIG. 16. In that example, a reservoir of heat exchange fluid is placed in contact with a heater or cooler, for example thermoelectric coolers (TEC) located within the controller box 600 but not illustrated. A source of heat exchange liquid 602, for example saline, is attached the reservoir to supply heat exchange fluid to the system. A pump within the controller box circulates the fluid through the reservoir and out the outflow line 604 which directs the heated or cooled fluid to the inflow port 82 of the catheter. After the fluid circulates through the catheter as described earlier, it returns to the reservoir through the inflow line 606, which receives fluid from the outflow port 84 of the catheter hub. The fluid is then circulated through the reservoir in contact with the heater or cooler, which heats or cools the fluid, and is then recirculated in a closed loop back through the catheter.

Temperature probes 608, 610 are placed on or in the patient so that they generate a signal that represents the temperature of the patient of the portion of the patient that is controlled by the system. A single probe may be used, but dual probes may also be used, for example to provide for redundancy as a safety measure. Those probes may be tympanic temperature probes, esophageal probes, rectal probes, temperature probes for measuring the temperature of the patient's blood, myocardial temperature probes, or any other probes that will generate a signal representative of the temperature sought to be controlled by the system which may be, for example, a temperature of a target tissue or core body temperature. Skin temperature probes are generally not sufficiently accurate or free from environmental influences to act as control probes for this system. However there is no fundamental reason why such probes could not be used, and if they were sufficiently accurate, even surface temperature probes would suffice.

A series of desired control parameters are manually input into a microprocessor control unit such as a dedicated computer in the control unit, via the user input interface 612. The parameters may include for example, the desired patient temperature and the rate of warming or cooling. The temperature probes 610, 608 provide patient temperature signals to the temperature input terminals 614, 616. The computer then controls the temperature of the heat exchange fluid based on the desired parameters as input by the user and the temperature signal as input by the temperature probes. The controller might, for example, add heat to the heat exchange fluid to either warm the patient or reduce the rate of cooling. Similarly, the controller might reduce the temperature of the heat exchange fluid to cool the patient or to reduce the rate of warming, depending on the current temperature of the heat exchange fluid and the desired parameters.

A method is also disclosed for warming, cooling or controlling a patient using the system disclosed here. That method entails placing a catheter of the invention with the heat exchange region in the bloodstream of a patient. Temperature probes are placed to sense the temperature of the patient or the target tissue in question. A controller is provided that can control the heat exchange between the catheter and the blood by, for example, controlling the temperature of heat exchange region. In the catheters of this invention that comprises controlling the temperature of or rate of flow of the heat exchange fluid provided to the heat exchange region. The controller's microprocessor is capable of receiving the signal representing the temperature of the patient and responding by controlling the heat exchange catheter to increase, decrease or maintain the temperature of the patient within precise parameters as input by the user.

A heat exchange device may also be supplied as a kit comprising the heat exchange device and a set of instruction for using the heat exchange device. The heat exchange device may comprise, for example, a heat exchange catheter as described in this application. The instructions for use will generally instruct the user to insert the heat exchange device into a body fluid containing region and to establish the temperature of the heat exchange device to affect the temperature of the body fluid. The instructions for use may direct the user to heat or cool the body fluid to achieve any of the purposes described in this application.

While all aspects of the present invention have been described with reference to the aforementioned applications, this description of various embodiments and methods shall not be construed in a limiting sense. The aforementioned is presented for purposes of illustration and description. It shall be understood that all aspects of the invention are not limited to the specific depictions, configurations or relative proportions set forth herein which depend upon a variety of conditions and variables. The specification is not intended to be exhaustive or to limit the invention to the precise forms disclosed herein. Various modifications and insubstantial changes in form and detail of the particular embodiments of the disclosed invention, as well as other variations of the invention, will be apparent to a person skilled in the art upon reference to the present disclosure. It is therefore contemplated that the appended claims shall cover any such modifications or variations of the described embodiments as falling within the true spirit and scope of the invention.

What is claimed is:

1. A heat exchange catheter for heating or cooling at least a portion of the body of a human or animal patient, said heat exchange catheter comprising:
   a catheter shaft having an inflow lumen and an outflow lumen extending longitudinally therethrough, said outflow lumen being separate from said inflow lumen; and
   at least one heat exchange balloon element comprising a plurality of expandable tubes helically disposed about the catheter shaft, said expandable tubes being fluidly connected to the inflow and outflow lumens such that heat exchange fluid may circulate in the inflow lumen, through the expandable tubes and out of the outflow lumen, the circulation of fluid through said expandable tubes causing the expandable tubes to expand to an expanded configuration;
   the balloon element being insertable into the vasculature of the patent patient and having a curvilinear configuration when heat exchange fluid is being circulated therethrough;
   wherein a first plug member forms a substantially fluid tight seal of the central lumen around the catheter shaft and a second plug member is located in the outflow lumen distal of the first plug member and forms a substantially fluid tight seal between the outflow lumen and the central lumen.

2. A heat exchange catheter according to claim 1 wherein said at least one balloon element comprises a plurality of balloon elements and, when heat exchange fluid is being circulated therethrough, at least one of the balloon elements assumes a curvilinear configuration about a common central axis.

3. A heat exchange catheter according to claim 2 wherein the balloon elements are spaced apart when heat exchange fluid is being circulated therethrough sufficient to allow blood to flow between the balloon elements.

4. A heat exchange catheter according to claim 2 wherein at least some of the balloon elements differ in size.

5. A heat exchange catheter according to claim 4 wherein at least one of the balloon elements is longer than another balloon element.

6. A heat exchange catheter according to claim 4 wherein at least one of the balloon elements is larger in diameter than another balloon element.

7. A heat exchange catheter according to claim 1 wherein the curvilinear configuration assumed by the balloon element when heat exchange fluid is being circulated therethrough comprises a generally helical configuration.

8. A heat exchange catheter according to claim 7 further comprising stand offs between the balloon elements to maintain spaces between the balloon elements when heat exchange fluid is being circulated therethrough.

9. A heat exchange catheter according to claim 7 wherein at least one balloon element, when in its generally helical configuration makes approximately 1 full rotation about a central axis per 2 to 4 inches of length.

10. A heat exchange catheter according to claim 1 wherein the at least one balloon element is twisted about a central tube that has a lumen extending longitudinally therethrough.

11. A heat exchange catheter according to claim 10 wherein the central tube has a proximal end and a distal end and at least one balloon element has a proximal end and a distal end, and wherein:

the lumen of the central tube is connected at its proximal end to the inflow lumen of the catheter shaft and at its distal end to the distal end of a balloon element, such that heat exchange fluid will flow through the inflow lumen, through the central tube and into that balloon element; and, the proximal end of that balloon element is connected to the outflow lumen of the catheter shaft such that heat exchange fluid will flow out of that balloon element and through the outflow lumen of the catheter shaft.

12. A heat exchange catheter according to claim 10 wherein the central tube has a proximal end and a distal end and at least one balloon element has a proximal end and a distal end, and wherein:

the proximal end of a balloon element is connected to the inflow lumen of the catheter shaft such that heat exchange fluid will flow through the inflow lumen and into the proximal end of that balloon element; and, the lumen of the central tube is connected to the distal end of that balloon element and the proximal end of the central tube is connected to the outflow lumen of the catheter shaft such that heat exchange fluid will flow from the distal end of that balloon element into the lumen of the central tube, through the lumen of the central tube and into the outflow lumen of the catheter shaft.

13. A heat exchange catheter according to claim 1 further comprising a distal manifold fluidly connecting the central lumen to the distal portions of the balloon elements.

14. A heat exchange catheter according to claim 1 further comprising a proximal manifold fluidly connecting the proximal portions of the balloon elements to the outflow lumen.

15. A heat exchange catheter according to claim 1 wherein at least a portion of the catheter shaft is insulated.

16. A heat exchange catheter according to claim 1 having a guidewire lumen extending longitudinally through at least a portion of the catheter.

17. A heat exchange catheter according to claim 16 wherein the at least one balloon element is helically disposed about a central member, said central member being attached to and extending coaxially from the catheter shaft and wherein the guidewire lumen nude trough the catheter shaft and trough the central member.

* * * * *